(12) United States Patent
Barhoum et al.

(10) Patent No.: US 11,696,877 B2
(45) Date of Patent: *Jul. 11, 2023

(54) GEL NETWORK HAIR TREATMENT COMPOSITIONS WITH REDUCED ODOR

(71) Applicant: Noxell Corporation, Hunt Valley, MD (US)

(72) Inventors: Moussa Barhoum, Frankfurt (DE); Pascale Smets, Strombeek-Bever (BE); Frank Veverka, Zwingenberg (DE); Manfred Schmitt, Bensheim (DE); Ingrid Merere, Darmstadt (DE); Christine Marie Cahen, Bonn (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/327,242

(22) PCT Filed: Sep. 6, 2017

(86) PCT No.: PCT/US2017/050309
§ 371 (c)(1),
(2) Date: Feb. 21, 2019

(87) PCT Pub. No.: WO2018/048924
PCT Pub. Date: Mar. 15, 2018

(65) Prior Publication Data
US 2019/0209441 A1   Jul. 11, 2019

(30) Foreign Application Priority Data

Sep. 6, 2016  (EP) .................................... 16187310

(51) Int. Cl.
| | | |
|---|---|---|
| *A61K 8/22* | (2006.01) | |
| *A61Q 5/10* | (2006.01) | |
| *A61Q 5/08* | (2006.01) | |
| *A61K 8/04* | (2006.01) | |
| *A61K 8/19* | (2006.01) | |
| *A61K 8/37* | (2006.01) | |
| *A61K 8/14* | (2006.01) | |
| *A61K 8/02* | (2006.01) | |
| *A61K 8/49* | (2006.01) | |

(Continued)

(52) U.S. Cl.
CPC ............ *A61K 8/042* (2013.01); *A61K 8/0295* (2013.01); *A61K 8/14* (2013.01); *A61K 8/19* (2013.01); *A61K 8/22* (2013.01); *A61K 8/342* (2013.01); *A61K 8/37* (2013.01); *A61K 8/39* (2013.01); *A61K 8/498* (2013.01); *A61K 8/55* (2013.01); *A61Q 5/08* (2013.01); *A61Q 5/10* (2013.01); *A61K 2800/87* (2013.01); *A61K 2800/88* (2013.01); *A61K 2800/882* (2013.01)

(58) Field of Classification Search
CPC ... A61Q 5/10; A61Q 5/08; A61Q 5/12; A61Q 5/06; A61Q 13/00; A61Q 5/00; A61Q 5/02; A61Q 5/065; A61K 2800/882; A61K 8/042; A61K 2800/48; A61K 8/55; A61K 2800/884; A61K 8/37; A61K 8/34; A61K 8/33; A61K 2800/56; A61K 8/86; A61K 2800/10; A61K 2300/00; A61K 8/00; A61K 2800/00; A61K 2800/88; A61K 8/22; A61K 2800/432

See application file for complete search history.

(56) References Cited

U.S. PATENT DOCUMENTS

2003/0226217 A1*  12/2003  Bowes .................... A61K 8/556
                                                                8/405
2006/0078528 A1*  4/2006   Yang ........................ A61Q 5/12
                                                                424/70.27

(Continued)

FOREIGN PATENT DOCUMENTS

| EP | 0435012 A1 | 7/1991 |
|---|---|---|
| EP | 2859880 A1 | 4/2015 |

(Continued)

OTHER PUBLICATIONS

"European Application Serial No. 16187310.4, Communication Pursuant to Article 94(3) EPC dated Feb. 6, 2019", 7 pgs.

(Continued)

*Primary Examiner* — Tracy Liu
(74) *Attorney, Agent, or Firm* — Dennemeyer & Associates, LLC; Victoria Friedman; Shawn E. Duckworth

(57) ABSTRACT

The invention relates to a hair colouring and/or bleaching composition comprising at least a first aqueous component (i) and a second aqueous component (ii) being mixed prior to application onto hair, wherein the first component (i) or the second component (ii) or both components (i) and (ii) comprise a gel-network system consisting of multi-lamellar sheets and vesicles with d-spacing (interlayer spacing between sheets) between 5 nm and 50 nm, preferably 10 nm to 30 nm, more preferred 15 nm to 25 nm as measured by Small Angle X-Ray Scattering (SAXS), and the first component (i) or the second component (ii) or both comprise at least a first malodor suppressant being a compound having a distribution coefficient log P of 2 or more and a molecular weight of between 100 and 400, a method for coloring or bleaching hair, a kit comprising the above components and the use of the described hair coloring composition for colouring and/or bleaching hair with a reduced or eliminated ammonia odour.

13 Claims, 4 Drawing Sheets

(51) Int. Cl.
    *A61K 8/34*     (2006.01)
    *A61K 8/39*     (2006.01)
    *A61K 8/55*     (2006.01)

(56) References Cited

U.S. PATENT DOCUMENTS

| | | | |
|---|---|---|---|
| 2006/0207037 A1 | 9/2006 | Fadel et al. | |
| 2006/0260072 A1* | 11/2006 | Lim | A61Q 5/10<br>8/405 |
| 2008/0010754 A1* | 1/2008 | Bureiko | A61K 8/19<br>8/406 |
| 2009/0226389 A1* | 9/2009 | Warr | A61Q 5/10<br>424/62 |
| 2013/0095056 A1* | 4/2013 | Murray | A61K 8/342<br>424/70.9 |

FOREIGN PATENT DOCUMENTS

| | | |
|---|---|---|
| EP | 2974712 A1 | 1/2016 |
| WO | WO-2005110499 A1 | 11/2005 |
| WO | WO-2016058710 A1 | 4/2016 |
| WO | WO-2018048924 A1 | 3/2018 |

OTHER PUBLICATIONS

"European Application Serial No. 16187310.4, Extended European Search Report dated Jan. 9, 2017", 10 pgs.

"European Application Serial No. 16187310.4, Office Action dated Sep. 30, 2016", 3 pgs.

"European Application Serial No. 16187310.4, Response filed Dec. 1, 2016 to Office Action dated Sep. 30, 2016", 13 pgs.

"International Application Serial No. PCT/US2017/050309, International Search Report dated Nov. 20, 2017", 5 pgs.

"International Application Serial No. PCT/US2017/050309, Written Opinion dated Nov. 20, 2017", 10 pgs.

"European Application Serial No. 16187310.4, Response Filed Jun. 17, 2019 to Communication Pursuant to Article 94(3) EPC dated Feb. 6, 2019", 22 pgs.

"International Application Serial No. PCT/US2017/050309, International Preliminary Report on Patentability dated Mar. 21, 2019", 10 pgs.

* cited by examiner

GEL NETWORK HAIR TREATMENT COMPOSITIONS WITH REDUCED ODOR

PRIORITY

This application is a U.S. National Stage Filing under 35 U.S.C. 371 from International Application No. PCT/US2017/050309, filed on Sep. 6, 2017, and published as WO 2018/048924 on Mar. 15, 2018, which application claims the benefit of priority from EP Patent Application No. 16187310.4, filed on Sep. 6, 2016, which are herein incorporated in their entirety by reference.

FIELD OF THE INVENTION

The present invention relates to a hair colouring and/or bleaching composition.

BACKGROUND OF THE INVENTION

The permanent alteration of the colour of keratinous fibers, in particular human hair, by the application of hair dyes is well known. In order to provide the consumer with the hair colour and the intensity of the colour desired, very complex chemical processes are utilized. Permanent hair colouring formulations typically comprise oxidative hair dye precursors, which can diffuse into the hair through the cuticle and into the cortex where they can then react with each other and suitable oxidizing agents to form the end dye molecule. Due to the larger size of these resultant molecules they are unable to readily diffuse out of the hair during subsequent washing with water and/or detergent; hence delivering a consumer-desired permanency of colour. This reaction typically takes place at pH from about 8.5 to about 10.5 (approximately pH 10) in the presence of an alkalizing agent and an oxidizing agent.

Despite the fact that commercial hair colouring products have been available for many years, the products still exhibit a number of consumer-related deficiencies.

Typically, permanent hair dye products will contain an alkaline compound or at least a compound generating an alkaline compound under specific circumstances, typically a source of ammonia. This serves the purpose of swelling the hair allowing the entry of the dye precursor molecules into the hair and also improves the lightening effect of the oxidizing agent, which is typically hydrogen peroxide. Ammonia shows the best hair colouring and/or bleaching performance as well as hair damage profile, versus alternative alkalizing agents. However, ammonia is also volatile and its associated odour is extremely unpleasant to the consumers of such products, particularly as these hair colouring and/or bleaching products are used in close proximity to the nasal region. Hence, it would be highly desirable to provide an oxidative hair colouring and/or bleaching composition, and kit thereof, which delivers the consumer required lightening level and colour but which has reduced or eliminated the detectable ammonia odour.

A number of attempts have been described in the literature to address the above identified improvement areas. For example, it has been described hair colouring and/or bleaching compositions comprising carbonate and/or carbamate compounds, it has also been described hair colouring and/or bleaching compositions comprising an alkalizing agent, alternative to ammonia and its salts, such as monoethanolamine. It has also been described to use compounds blocking and/or antagonizing the odour of ammonia. However these previous attempts have not proven fully satisfactory vis-à-vis further criteria, as they may exhibit a limited hair colouring and/or bleaching performance including limited colour delivery, uptake and/or durability; significant damages to the hair including brittle fibre formation.

SUMMARY OF THE INVENTION

The present invention relates to a hair colouring and/or bleaching composition comprising at least a first aqueous component (i) and a second aqueous component (ii) being mixed prior to application onto hair, wherein the first aqueous component (i) comprises, in a cosmetically acceptable carrier one or more oxidizing agent(s) and the second aqueous component (ii) comprises, in a cosmetically acceptable carrier one or more alkalizing agent(s) selected from the group consisting of ammonia, its salts and mixtures thereof wherein the first component (i) or the second component (ii) or both components (i) and (ii) comprise a gel-network system consisting of multi-lamellar sheets and vesicles with d-spacing (interlayer spacing between sheets) between 5 nm and 50 nm, including 10 nm to 30 nm, including 15 nm to 25 nm as measured by Small Angle X-Ray Scattering (SAXS), and the first component (i) or the second component (ii) or both comprise at least a first malodor suppressant being a compound having a distribution coefficient log P of 2 or more and a molecular weight of between 100 and 400 or a at least first and a second malodor suppressant, both being a compound having a distribution coefficient log P of 2 or more and a molecular weight of between 100 and 400. It also relates to kit, method and use thereof. The present invention provides superior hair treatment performance, particularly superior colouring and bleaching performance, with a reduced or even eliminated smell of one or more malodourous active ingredients upon application.

There is the need thereof for providing a composition comprising ammonia and/or its salts thereof, which releases a reduced or no odour, especially upon application onto hair. There is also the need for providing a composition comprising ammonia and/or its salts thereof, which releases a reduced or no odour, while containing sufficiently high amounts of ammonia in order to provide superior hair treatment performance. There is also the need for providing a composition comprising ammonia and/or its salts thereof, releasing a reduced or no odour, without imparting significant damages onto the hair fibers.

Particularly, there is the need thereof for providing a composition releasing a reduced or no ammonia odour, upon application onto hair. There is also the need for providing a composition releasing a reduced or no ammonia odour, while providing superior hair colouring and bleaching performance. There is also the need for providing a composition releasing a reduced or no ammonia odour, without imparting significant damages onto the hair fibers.

It has now been found that the use of specific malodor suppressants in a composition for hair treatment which is prone to the release of malodorous substances such as ammonia, and which comprises a gel-network system, results in a significant decrease of malodor release and especially a significant decrease in malodor perception of the user of such a hair treatment composition. The finding according to the present invention is especially useful in hair treatment compositions such as hair colouring compositions or hair bleaching compositions.

In one aspect, the present invention relates to a hair colouring and/or bleaching composition comprising at least a first aqueous component (i) and a second aqueous component (ii) being mixed prior to application onto hair, wherein:

the first aqueous component (i) comprises, in a cosmetically acceptable carrier one or more oxidizing agent(s) and the second aqueous component (ii) comprises, in a cosmetically acceptable carrier one or more alkalizing agent(s) selected from the group consisting of ammonia, its salts and mixtures thereof, wherein the first component (i) or the second component (ii) or both components (i) and (ii) comprise a gel-network system consisting of multi-lamellar sheets and vesicles with d-spacing (interlayer spacing between sheets) between 5 nm and 50 nm, preferably 10 nm to 30 nm, more preferred 15 nm to 25 nm as measured by Small Angle X-Ray Scattering (SAXS), and the first component (i) or the second component (ii) or both comprise at least a first malodor suppressant being a compound having a distribution coefficient log P of 2 or more and a molecular weight of between 100 and 400 or a at least first and a second malodor suppressant, both being a compound having a distribution coefficient log P of 2 or more and a molecular weight of between 100 and 400.

In another aspect, the present invention relates to a hair colouring or bleaching kit comprising an individually packaged first aqueous component (i) comprising, in a cosmetically acceptable carrier one or more oxidizing agent(s) and an individually packaged second aqueous component (ii) comprising in a cosmetically acceptable carrier one or more alkalizing agent(s) selected from the group consisting of ammonia, its salts and mixtures thereof, wherein the first component (i) or the second component (ii) or both components (i) and (ii) comprise a gel-network system consisting of multi-lamellar sheets and vesicles with d-spacing (interlayer spacing between sheets) between 5 nm and 50 nm, including 10 nm to 30 nm, including 15 nm to 25 nm as measured by Small Angle X-Ray Scattering (SAXS), and the first component (i) or the second component (ii) or both comprise at least a first malodor suppressant being a compound having a distribution coefficient log P of 2 or more and a molecular weight of between 100 and 400 or at least a first and a second malodor suppressant, both being a compound having a distribution coefficient log P of 2 or more and a molecular weight of between 100 and 400.

In still another aspect, the present invention relates to a method of treating hair comprising the steps of applying a composition after mixing of two components according to the invention or a composition obtainable as a mixture from a kit according to the invention to the hair, leaving said composition on the hair for from 2 to 60 minutes and subsequently rinsing said composition from the hair.

In still another aspect, the present invention relates to a method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition according to the invention or obtainable as a mixture from a kit according to the invention, applying said composition to the hair and retaining said composition on the hair for a time period of less than 20 minutes and subsequently rinsing said composition from the hair. In another aspect, the present invention relates to the use of said composition and/or kit for colouring and/or bleaching hair with a reduced or no ammonia odour.

DETAILED DESCRIPTION OF THE INVENTION

Figure 1:
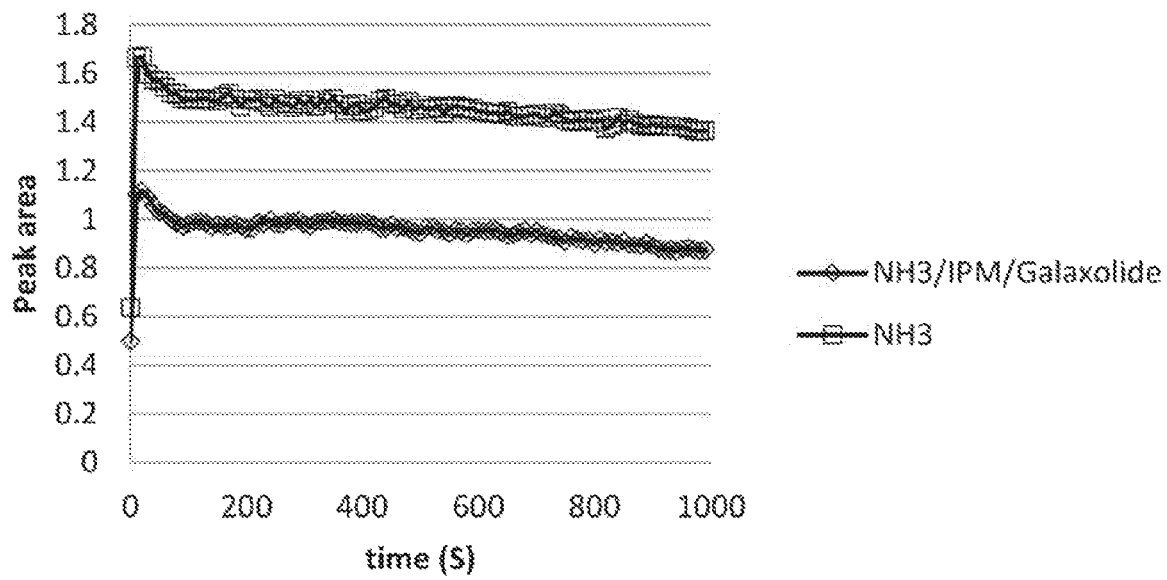
FIG. 1 shows the ammonia release kinetic of the 2.41% NH3 solution and the 2.15% NH3 solution with Galaxolide/ IPM without stirring in the vessel (Examples 1 and 2). The sample with IPM/Galaxolide shows a lower ammonia release. Since a film of the nonpolar liquid was observable on the solution, it might be a physical effect.

As used herein the term "hair" to be treated may be "living" i.e. on a living body or may be "non-living" i.e. in a wig, hairpiece or other aggregation of non-living keratinous fibers. Mammalian, such as human hair is preferred. However wool, fur and other keratin containing fibers are suitable substrates for the compositions according to the present invention.

By "hair colouring" composition, it is meant a composition suitable for changing the colour of hair.

The hair colouring composition is referred hereinafter as "the composition", unless otherwise specified. The hair colouring composition may comprise oxidative dye precursors, direct dyes or even no, or substantially no, dyes in case of bleaching only compositions where the change of colour is mainly caused by the degradation of the natural melanin contained in the hair shaft by the oxidizing agent. The term "hair colouring" composition as used herein covers hair bleaching and hair oxidative dyeing products.

All percentages are by weight of the final hair treatment composition (hair colouring composition or hair treatment composition), i.e. of the ready-to-use composition which is the composition to be applied on hair, unless otherwise specified. When a ready-to-use composition is prepared by mixing two or more components comprising ingredients to be mixed for the desired effect, the amount of these ingredients is can also provided based on the weight of the component comprising such an ingredient, in case of the present text, e.g., component i) and component ii).

When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

In a first aspect, the present invention relates to a hair colouring and/or bleaching composition comprising at least a first aqueous component (i) and a second aqueous component (ii) being mixed prior to application onto hair.

The first aqueous component (i) and the second aqueous component (ii) may be mixed prior to application to hair in a ratio ranging from 5:1 to 1:5, e.g., from 3:1 to 1:3 or from 2:1 to 1:2, in some cases they may be mixed in a ratio of about of 1:1 The first aqueous component (i) is often called "developer", and comprises, in a cosmetically acceptable carrier one or more oxidizing agent(s). Any oxidizing agent known in the art may be used. Preferred oxidizing agents are water-soluble peroxygen oxidizing agents. As used herein "water-soluble" means that in standard conditions at least 0.1 g, including 1 g, including 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

The first aqueous component may comprise a total amount of oxidizing agents ranging from 0.1% to 12%, alternatively from 1% to 9%, alternatively from 2% to 6%, by total weight of the composition.

Suitable water-soluble oxidizing agents include, but are not limited to: inorganic peroxygen materials capable of yielding hydrogen peroxide in an aqueous solution. Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

In a specific embodiment, the composition comprises a water-soluble oxidizing agent selected from the group consisting of hydrogen peroxide, percarbonates (which may be used to provide a source of both oxidizing agent and carbonate ions and or ammonium ions), persulphates, and mixtures thereof; alternatively a water-soluble oxidizing agent being hydrogen peroxide.

The second aqueous component (ii), generally called "tint," comprises, in a cosmetically acceptable carrier one or more alkalizing agent(s) selected from the group consisting of ammonia, its salts and mixtures thereof. The group can, e.g., consist of ammonia, ammonium halides, ammonium sulfate, ammonium phosphate, ammonium lactate, ammonium glycinate, ammonium aspartate, ammonium nitrate, ammonium perchlorate, ammonium carbonate, ammonium hydrogen carbonate, ammonium silicate, ammonium borate, and mixtures of two or more thereof. The group can further consist of ammonia, ammonium carbonate, and mixtures thereof; It can be preferred, if the alkalizing agent is ammonia or the alkalizing agent is ammonium carbonate. If both present, the ammonium ions and the carbonate ions are present in the second aqueous component (ii) at a weight ratio of from 3:1 to 1:10, alternatively from 2:1 to 1:5.

The second aqueous component (ii) may comprise a total amount of alkalizing agents ranging from 0.1% to 10%, alternatively from 0.5% to 6%, alternatively from 1% to 4%, by total weight of the composition.

According to the invention the first component (i) or the second component (ii) or both components (i) and (ii) comprise a gel-network system consisting of multi-lamellar sheets and multi lamellar vesicles both showing a d-spacing (interlayer spacing between sheets) between 5 nm and 50 nm, preferably 10 nm to 30 nm, more preferred 15 nm to 25 nm as measured by Small Angle X-Ray Scattering (SAXS).

The presence of multi-lamellar sheets and multi lamellar vesicles is generally easily confirmed via electron microscopy. Multi-lamellar sheets can usually be observed as elongated sheet like structures, which can be essentially straight or slightly curved or bent. Multi lamellar vesicles are observable as small, generally rounded or elliptical structures with a comparatively small spatial extension. It can be preferred according to the invention, when at least the second aqueous component comprises such a gel-network-system.

Generally, gel-network systems are well known. They are, e.g., available by heating a dispersion of a fatty alcohol in water with a surfactant to a temperature above the melting point of the fatty alcohol and mixing the dispersion. During the mixing process, the fatty alcohol melts, allowing the surfactant to partition into the fatty alcohol droplets. The surfactant transports water into the fatty alcohol droplets. This changes the isotropic fatty alcohol drops into liquid crystalline phase drops. When the mixture is cooled below the melt temperature of the formed liquid crystal phase the liquid crystal phase is converted into a crystalline gel network phase. The gel-network may in some cases not yet be completely formed immediately after the end of the mixing process, but will develop over a short period of time, e.g., in some cases after 1 to 10 hours, in some cases after 10 to 48 hours or in some cases after 2 to 5 days or even longer periods of up to 10 days.

In one embodiment, if a component according to the invention comprises a fatty alcohol in order to form a liquid crystalline gel-network phase. The fatty alcohol may be selected from the group consisting of linear and/or branched C12 to C30 fatty alcohols, i.e., fatty alcohols with 12, 14, 16, 18, 20, 22, 24, 26, 28 or 30 carbon atoms in the carbon chain or a mixture of two or more of such alcohols. The range of advantageous chain lengths can be from C14 to C28 or from C14 to C26; e.g., the fatty alcohol can be chosen from the group consisting of cetyl alcohol, stearyl alcohol, cetearyl alcohol, behenyl alcohol, any mixtures of two, three or more thereof. The component may comprise from 0.5% to 20%, alternatively from 2% to 10%, alternatively from 4% to 8%$_1$ of fatty alcohol by total weight of the composition. The amount of each particular fatty alcohol or mixtures thereof described herein before can account for up to 100% (or 100%) of the total amount of fatty alcohol(s) in the composition.

The composition comprises a non-ionic surfactant. The non-ionic surfactant may be selected from the group consisting of polyoxyethylene C12 to C30 alkyl ethers, i.e., from alkyl ethers of fatty alcohols having 12, 14, 16, 18, 20, 22, 24, 26, 28 or 30 carbon atoms in the carbon chain, e.g. polyoxyethylene C14 to C28 alkyl ethers or polyoxyethylene C14 to C26 alkyl ethers. It can be preferred if the non-ionic surfactant is selected from the group consisting of polyoxyethylene C12 to C30 alkyl ethers having at least 2 ethylene oxide units, e.g., from the group consisting of polyoxyethylene C12 to C30 alkyl ethers, e.g. polyoxyethylene C14 to C28 alkyl ethers or polyoxyethylene C14 to C26 alkyl ethers, having from 20 to 300 or from 25 to 200 or from 50 to 200 ethylene oxide units, or from the group consisting of polyoxyethylene C12 to C30 alkyl ethers, e.g. polyoxyethylene C14 to C28 alkyl ethers or polyoxyethylene C14 to C26 alkyl ethers, having from 100 to 200 ethylene oxide units, e.g., from the group consisting of ceteareth-25, steareth-20, steareth-100, steareth-150, steareth-200, and mixtures of two or more thereof. Other non-ionic surfactants which can optionally be used according to the invention are polyethyleneglycol fatty acid esters, poly oxy ethylene castor oil, polyoxyethylene hydrogenated castor oil, polyoxyethylene fatty amides and their monoethanolamine and diethanolamine derivatives and polyethoxylated fatty amines, and mixtures thereof.

Alternatively, the non-ionic surfactant(s) may be free of polyethyleneoxide chains. Representative examples of non-ionic surfactants free of polyethyleneoxide chains include polyglycerolated fatty acids, polyglycerolated fatty amides, polyglycerolated alkyl phenols, polyglycerolated [alpha]-diols, polyglycerolated alcohols, alkyl polyglucosides, sugar esters and mixtures thereof.

The composition may comprise from 0.1% to 5%, e.g., from 0.2% to 3%, or from 0.4% to 1.5%, of non-ionic surfactant by total weight of the overall composition. As all nonionic surfactants may be present in one of components (i) or (ii) it may thus be that component (i) comprises from 0.14, to r e.g., from 0.2% to 3%, or from 0.4% to 1.5%, of non-ionic surfactant or component (iI) comprises from 0.1% to 5%, e.g., from 0.2% to 3%, or from 0.4% to 1.5%, of non-ionic surfactant.

Any of the components (i) or (ii) or both may, in some cases, comprise a phosphate ester compound selected from the group consisting of alkyl phosphate esters, alkoxylated alkyl phosphate esters, and mixtures thereof. The phosphate ester compound may be selected from the group consisting of C12 to C30 alkyl phosphate esters, alkoxylated C12 to C30 alkyl phosphate esters, and mixtures thereof, e.g., from the group consisting of C12 to C18 alkyl phosphate esters, alkoxylated C12 to C18 alkyl phosphate esters, and mixtures thereof, or from the group consisting of oleth-3 phosphate, oleth-5 phosphate, oleth-10 phosphate, cetoleth-5 phosphate, cetoleth-10 phosphate, trideceth-5 phosphate, trideceth-6 phosphate, trideceth-10 phosphate, cetyl phosphate, dicetyl phosphate, oleyl phosphate, dioleyl phosphate, stearyl phosphate, C9-15 alkyl phosphate, ceteareth-2 phosphate, ceteareth-20 phosphate, ceteth-10 phosphate, deceth-4 phosphate, glycereth-26 phosphate, PPG-5-ceteth-10 phosphate, steareth-2 phosphate, DEA-oleth-3 phosphate, DEA-oleth-3 phosphate, PEG-5 ethylhexyl ether phosphate, and mixtures thereof, or from the group consisting of PPG-5-ceteth-10 phosphate, oleth-3 phosphate, oleth-10 phosphate, ceteth-10 phosphate, dicetyl phosphate, cetyl phosphate, stearyl phosphate, ceteareth-2 phosphate, and mixtures thereof or from the group consisting of ceteth-10 phosphate, dicetyl phosphate, ceteareth-2 phosphate, and mixtures thereof. It is also possible that a component comprises mixtures of two or more compounds from two or more alternative groups.

Commercially suitable raw materials include materials of the Crodafos™ Series from Croda, particularly Crodafos™ CES, Crodafos™ CS2A. Crodafos™ CES comprises cetearyl alcohol, dicetyl phosphate, ceteth-10 phosphate. Crodafos™ CS2A comprises ceteareth-2-phosphate. The composition may comprise from 0.01% to 40%, alternatively from 0.1% to 20%, alternatively from 1% to 10%, alternatively from 2% to 8% of the phosphate ester compound by total weight of the composition.

It can be preferred that the composition is free of any phosphate ester compound other than the phosphate ester compound selected from the group consisting of alkyl phosphate esters, alkoxylated alkyl phosphate esters, and mixtures thereof.

The fatty alcohol, the non-ionic surfactant, and the optional phosphate ester compound are comprised, in part or all, in a gel network system. The gel network significantly contributes in reducing, or even eliminating, the ammonia odour, when combined with the specific malodour reducing compounds described hereinafter.

From 50% to 100%, alternatively from 70% to 100%, alternatively from 90% to 100%, alternatively substantially 100% of the fatty alcohol present in the composition can be comprised within the gel network. From 50% to 100%, alternatively from 70% to 100%, alternatively from 90% to 100%, alternatively substantially 100% of the nonionic surfactant present in the composition is comprised within the gel network. From 50% to 100%, alternatively from 70% to 100%, alternatively from 90% to 100%, alternatively substantially 100% of the phosphate ester compound present in the composition is comprised within the gel network. The amount of fatty alcohol in the gel network can, e.g., be determined by DSC measurements.

The first component (i) or the second component (ii) or both comprise at least a first malodor suppressant being a compound having a distribution coefficient log P of 2 or more and a molecular weight of between 100 and 400 or a at least first and a second malodor suppressant, both being a compound having a distribution coefficient log P of 2 or more and a molecular weight of between 100 and 400.

In the fields of organic and medicinal chemistry, a partition (P) coefficient is the ratio of concentrations of a compound in the two phases of a mixture of two immiscible solvents at equilibrium. Hence these coefficients are a measure of differential solubility of the compound between these two solvents. One of the solvents chosen is water while the second is octanol. Hence the partition coefficient is a measure of how hydrophilic ("water loving") or hydrophobic ("water fearing") a chemical substance is. The partition coefficient is the ratio of concentrations of un-ionized compound between the two solutions. The logarithm of the ratio of the concentrations of the un-ionized solute in the solvents is called log P:

$$\log P_{oct/wat} = \log\left(\frac{[\text{solute}]_{octanol}}{[\text{solute}]_{water}^{un\text{-}ionized}}\right).$$

It can be preferred if in a hair colouring and/or bleaching composition according to the invention the first malodor suppressant or the first and the second malodor suppressant comprise at least one functional group selected from the group consisting of keto group, aldehyde group, ether group, ester group or hydroxyl group or two or more of such groups, either of the same type or of one or more different types.

While generally all types of malodor suppressants according to the teaching of the present invention provide for a reduced malodor of the claimed hair colouring and/or bleaching composition, it has proven to be advantageous in many cases if at least the first malodor suppressant has a log P (octanol/water) of less than 9. This can also be advantageous if only one malodor suppressant is present.

Apart from the successful use of a single malodor suppressant, it is also possible that a hair colouring and/or bleaching composition according to the invention comprises a first malodor suppressant being a compound having a distribution coefficient log P (octanol/water) of 2 or more and a molecular weight of between 100 and 400 and at least a second malodor suppressant being a compound having a distribution coefficient log P (octanol/water) of 3 or more and a molecular weight of between 100 and 400, the first malodor suppressant and the second malodor suppressant being different compounds and at least one of the first and second malodor suppressants being liquid at 23° C. and 1013 mbar and the first and second malodor suppressant forming a solution upon mixing.

Generally, it has proven to be successful if the first malodor suppressant or the first and second malodor suppressants are selected from the group consisting of (hereinafter called: list of malodor suppressants) isopropylmyristate, galaxolide, habanolide, Operanide, Okoumal, Silkolide, Musk Plus, Helvetolide, Romandolide, Celestolide, Scentenal, HIYDROXYCITRONELLAL, o-Cresol, Para Cresol, linalool oxide (furanoid), Coumarone, METHYL BENZOATE, Canthoxal, Cyclopidene, Methyl Octalactone, ISO BUTAVAN, Ethyl valerate, natural (US), Hexyl Aldehyde, BENZYL METHYL ETHER, Isopimpinellin, HYDROXYOL, TRIFERNAL, p-Tolyl acetate, ALLYL PHENOXY ACETATE, METHYL ANTHRANILATE, Eugewhite, 4-PHENYL-2-BUTANOL, Dihydroisophorone, Gardamide, 3-Hexenyl acetate, CIS 3 HEXENYL ACETATE, CYCLOHEXYL ETHYL ALCOHOL, PHENOXL ETHYL PROPIONATE, 5-METHYL-3-HEPTANONE, 3-Heptanol, 4-Vinylphenol, METHYL AMYL KETONE, ISO PROPYL 2-METHYLBUTYRATE, METHYL HEPTENONE, 4-Ethylguaiacol, Ultravanil, Furfuryl methyl sulfide, Methyl Laitone, METHOXY MELONAL, DIMETHYL BENZYL CARBINOL, 2-ISOPROPYL-N,2,3-TRIMETHYLBUTYRAMIDE, BENZYL METHOXYETHYL ACETAL, Methoxyisobutylpyrazine, 2-ISOPROPYL-4-METHYL THIAZOLE, Benzoin, KOUMALACTONE, Pyranol, Indoflor Crist., FLOREX, trans-Cinnamic acid, Cinnamyl formate, KEONE, 8-HYDROXY PARA-CYMENE, LINALOOL OXIDE, Spirodecane, PHENYL ETHYL ACETATE, PHENYL ETHYL ACETATE, 2-ISOBUTYLTHIAZOLE, 2,4-dimethyl phenol, ETHYL TIGLATE, Ethyl Phenyl Acetate, BUCCOXIME, Verbenone, Verbenone, METHYL PHENYL, CARBINYL ACETATE, CINNAMALVA, Cinnamyl nitrile, OXANE, 4-Isopropylbenzyl alcohol, BENZYL PROPIONATE, 2-Heptanol, Methyl Cinnamate, ETHYL METHYL PHENYL GLYCIDATE, p-TOLYL ACETATE, HELIOTROPIN DIETHYL ACETAL, p-Butyrylphenol, Amyl Vinyl Carbinol, Agarbois, MUGUESIA, METHYL SALICYLATE SYNTHETIC, D-Dihydrocarvone, mixture of isomers, d-p-8(9)-Menthen-2-one, trans-Dihydrocarvone, INDOL, BENZYL ETHYL ETHER, NONALACTONE, Nonalactone, cis-Limonene oxide, METHYL JASMONATE, ETHYL 2 METHYL PENTANOATE, Pentanoic acid, 2-methyl-ethyl ester (S)-2, cis-Tagetone, EUGENOL, Hexyl formate, Nerolione, MONTAVERDI, CAMPHOR GUM, (5E)-2,6-Dimethyl-1,5,7-octatrien-3-ol, THUJONE, ETHYL AMYL KETONE, Longozal, Ionone Epoxide Beta, METHYL HEXYL KETONE, Methyl Lavender Ketone, 2,10-Epoxypinane, Amyl Acetate, AMYL-ACETATE (isomer blends), Butyl butyrate, Cis-6-Nonen-1-OL FCC, (E,Z)-3,6-nonadien-1-ol, 3,6-NONADIEN-1-OL, 3'6-NONadien-1-ol, PHENOXY ETHYL ISO BUTYRATE, 2,6-Nonadien-1-ol, CIS-3-HEPTENYL ACETATE, cis-3-HEXENYL PROPIONATE, Heptanal, Ocimenol, ISO EUGENOL ACETATE, (E)-Isoeugenol, cis-iso-Eugenol, ISO EUGENOL, MYRTENAL, DIMETHYL ANTHRANILATE, 3-Propylidenephthalide, 4-METHYL QUINOLINE, Para Methyl Quinoline, ALLYL AMYL GLYCOLATE, CINNAMYL ACETATE, cis-Sabinol, DL-BORNEOL, iso borneol, PERILLA ALDEHYDE, skatole, 4-Ethylphenol, P-ETHYL PHENOL, Eugenyl Acetate, Hydratropic Aldehyde Dimethyl Acetal, 2,6-Nonadien-1-al, E Z-2,6-Nonadien-1-al, e,e,-2,6-NONADIEN-1-AL. Myristicin, Leaf acetal, Leguminal, Azurone, alpha-Fenchyl Alcohol, FRUCTALATE, DIHYDRO EUGENOL, trans,trans-2,4-Nonadienal, L-Fenchone, fenchone, 3,5,5-Trimethyl-1-hexanol, DIHYDROTAGETONE, 3-Methyl-4-phenylpyrazole, Aladinate, Cyclohexyl acetate, PLICATONE, 1-Oxaspiro[5,5]undecan-4-ol, 4-methyl-, Myroxide, 1-phenyl-2-pentanol, 4-THUJANOL, Heptyl alcohol, Heptyl alcohol, Livescone, DECAHYDRO-2-NAPHTHOL, Asarone, PHENYL ETHYL DIMETHYL CARBINOL, METHYL ISO EUGENOL, PARA CRESYL METHYL ETHER, Isoamyl isobutyrate, MYRCENOL SUPER, GAMMA DECALACTONE, SAFROLE, DIETHYLPHTHALATE, DELTA DECALACTONE, Methyl Eugenol, Para Cresyl iso-Butyrate, CIS JASMONE, 2-PHENYL-3-(2-FURYL)PROP-2-ENAL, Phenethyl propionate, Melozone, Octanol-3, INDOCOLORE, Methoxycitronellal PG, Rhodinol 70, Jasmacyclene, VIOLIFF, 4-PENTENOPHENONE, d-CARVONE (SYNTHETIC) FCC, L CARVONE, L-CARVONE, BENZYL BUTYRATE, RINGONOL 50 TEC, PROPENYL GUAETHOL, 3-Cyclohexene-1-methanol, 3,5-dimethyl-, Clarycet, DELPHONE, ISO CYCLO CITRAL, beta-Terpineol, HEXYL ACETATE, Benzyl Iso Butyrate, STYRALLYL PROPIONATE, Amyl Propionate, AMYL PROPIONATE, ETHYL CAPROATE FCC, Ethyl Hexyl Ketone, DEHYDROXY LINALOOL OXIDE, TRIPLAL EXTRA, triplal extra, ETHYL CINNAMATE, cumin acetaldehyde, Plinol, Lyral, EUCALYPTOL, Anapear, 1-ethyl-3-methoxytricycloheptane, Cyclohexylmagnol, Dipropyl sulphide, METHYL DIHYDRO JASMONATE, trans-Hedione, 3,5,5-Trimethylhexanal, ISO PENTYRATE, CYCLO GALBANATE, BUTYL BUTYRYL LACTATE FCC, cis-Carveol, 1-Carveol, (+)-Dihydrocarveol, DIHYDROCARVEOL, Iso Pulegol, DIHYDRO ISO JASMONATE, LRG, Herboxane, 3,5,5-TRIMETHYLCYCLOHEXANOL, ISO-AMYL BUTYRATE, Efetaal, Cantryl, ZENOLIDE, Isononanol, DIMETOL, VERDURAL B EXTRA, BENZOPHENONE, PHENYL HEXANOL, CAPRYLIC ACID (NATURAL), Isobutyl angelate, ROSAPHEN, Dimethyl Octenone, LIGUSTRAL OR TRIPLAL, para-menth-3-en-1-ol, DIHYDROTERPINEOL, PATCHON, trans-2-tert-Butylcyclohexanol, VERDOL, 2(10)-PINEN-3-OL, Fruitnat, OCTYL ALCOHOL, Magnolan, ETHYL SALICYLATE, MEFRANAL, SCLAREOLATE®, Syvertal, piperitenone, HERBAC, Milk Lactone, Menthone gliceriool ketal, ALPHA TERPINEOL, Alpha Terpineol Supra, MAJANTOL, MAJANTOL, TERPINEOL, METHYL BETA-NAPHTHYL KETONE, Octanenitrile, trans-Ocimenone, Peacholide, Rosyrane Super, delta-UNDECALACTONE FCC, Romascone, 4-Carvomenthenol, Terpinenol-4, Cinnamyl propionate, 2-SEC-BUTYL CYCLO HEXANONE, MENTHONE GLYCERIN ACETAL, CARVACROL, Thymol Crystals, ANETHOLE USP, TRANS ANETHOLE, BROMSTYROL, METHYL HEPTINE CARBONATE, LRG, PHENYL ET-YL METHYL ETHYL CARBINOL, Allyl phenethyl ether, DIHYDRO MYRCENOL, RHUBOFIX, Hydrocitronitrile, CYCLOPENTOL HC, LRG, PERILLA ALCOHOL, 2,6-Octadienal,_3,7-dimethyl-,_(E)-, CITRAL, Phenethyl butyrate, (R)-(–)-Pulegone, Isocyclogeraniol, CUMINIC ALDEHYDE, ISO BUTYL PHENYLACETATE, 1,4-Cineole, FG, MELONAL, Estragol Ex Badiane, Petiole, ROSSITOL, (+)-D-Menthol, d-Neo-menthol, LAEVO MENTHOL, MENTHOL NATURAL, Menthol Racemic, neo-Menthol, 2,2,5-

Trimethyl-4-hexenal, Isopropyl Quinoline, MAYOL, ETHYL OENANTHATE, Hexyl propionate, Amyl butyrate, mixture of isomers, CIS 3 HEXENYL BUTYRATE, 2 Nonen-1-al, Nonenal, ISO MENTHONE, Isomenthone, MENTHONE RACEMIC, FLOROPAL, 1-Hepten-1-ol, 1-acetate, (R)-gamma-Undecalactone, (S)-gamma-Undecalactone, UNDECALACTONE, Jasmatone, Dihydro Cyclacet, 5-PHENYL-3-METHYL-2-PENTENONITRILE, Citronitril, ISODIHYDRO LAVANDULAL FCC, 7-Ethoxy-3,7-dimethyloctanal, gamma-Terpineol, ROSALVA, Tetrahydrojasmone, Damascol 4-, 6-HYDROXYDIHYDROTHEASPIRANE, 2-Nonanol, PHENYL ETHYL ISO BUTYRATE, OCTYL ALDEHYDE, Muguol, Violet Nitrile, Orivone, P-TERT-AMYLCYCLOHEXANOL, Verdalia A, Vivaldie, LACTOJASMON, Benzyl isovalerate, CORANOL, laevo-linalool, LINALOOL, S)-(+)-Linalool, 2-nonanone, RHUBOFLOR, TETRA HYDRO LINALOOL, TETRA HYDRO MUGUOL, TETRAHYDRO-4 METHYL-2 PHENYL-2-PYRAN, Phenylethyl methacrylate, Reseda Body, 4-Chloro-3,5-Xylenol, VERDYL PROPIONATE, (+)-Lavandulol, (R)-(−)-Lavandulol, Gelsone, DIMETHYL BENZYL CARBINYL ACETATE, Isoamyl angelate, CYCLEMAX, CITROWANIL B, PELARGENE, ALLYL CAPROATE, Para Tertiary Butyl Phenol, SPIRO [FURAN-2(3H),5'-(4,7-METHANO-5H-INDENE], DECAHYDRO, Dihydroanethole, Corps Racine VS, Opalal®, OXADIENE, Cumin Nitrile, METHYL PAMPLEMOUSSE, Nonadyl, Acetal R, Benzyl Cinnamate, CITRONELLYL NITRILE, JASMOPYRANE, 3-hexen-1-yl isovalerate, CIS-3-HEXENYL ALPHA METHYL BUTYRATE, GERANIOL, GERANIOL, Methyl camomille, NEROL, DIMETHYL OCTANOL, DIMETHYL OCTANOL, CYCLOMETHYLENE CITRONELLOL, Cinnamyl isobutyrate, gamma-ionone, Undecanolide, DAMASCONE GAMMA, Nopylaldehyde, (d)-Citronellal, (l)-Citronellal, CITRONELLAL, Mugetanol, Hexenyl tiglate, 1,2-Dihydrolinalool, dihydro-Linalool, ISO NONYL ACETATE, Cosmene, GERANYL FORMATE, NERYL FORMATE, FURFURYL HEXANOATE, Cyprisate Ci, METHYL OCTINE CARBONATE, Isoamyl phenyl ether, 2-hexylidene cyclopentanone, 10-UNDECEN-1-OL, RHUBAFURAN, CYCLABUTE, BETA NAPHTHOL METHYL ETHER, Heptyl acetate, Bornyl Acetate, ISO BORNYL ACETATE, ETHYLENE BRASSYLATE, PRENYL BENZOATE, LINALYL FORMATE, Vetiverol, VETIVEROL, HEXYL-2-FUROATE, Pomarose, Liminal, TABANON COEUR, DELTA DAMASCONE, Jasmonitrile, BARANOL, CITRONELLOL, R-(+)-B-CITRONELLOL, ISO JASMONE T, PARMAVERT, METHYL ISO BUTENYL TETRAHYDRO PYRAN, Rose Oxide L, Decenal-9, Octacetal, Iso Bergamate, IRALIA TOTAL, BENZYL BENZOATE, gamma-Dodecalactone, CYCLOBUTANATE, FRUITATE, Iso Butyl Caproate, cis-4-DECEN-1-AL-FCC, DECENAL (TRANS-4), Benzyl ether, hexyl butyrate, CITRONELLYL OXYACETALDEHYDE, delta-DODECALACTONE FCC, BUTYL BENZOATE, CYMAL, FLORHYDRAL, CITRAL DIMETHYL ACETAL, Hexyl Isobutyrate, NONYL ALDEHYDE, ETHYL SAFRANATE, Methyl geraniate, Cis-3-Hexenyl Valerate, ETHYL LINALOOL, Flor_acetate, Methyl Cyclogeranate, Isobutyl benzoate, CYCLOHEXYL ETHYL ACETATE, Claritone, p-t-Butyl phenyl acetaldehyde, Para Anisyl Phenyl Acetate, Bergamal, Citronellyl Formate, Phenyl Benzoate, Dihydrojasmone, Ethyl gamma-safranate, Pivarose, Geranyl Nitrile, Cis-3-Hexenyl Tiglate, ISO BUTYL SALICYLATE, ETHYL DAMASCENATE, ethyl isopropyl bicycloheptene-2-carboxylate, ISO BUTYL QUINOLINE, Isobutyl Quinoline-2, NEOBERGAMATE FORTE, 4-tert-Butylbenzaldehyde, gamma-Terpinyl acetate, Dispirone, N-ETHYL-2-ISOPROPYL-5-METHYLCYCLOHEXANE CARBOXAMIDE, 1-Methyl-3-methoxy-4-isopropylbenzene, ALLYL HEPTOATE, Citral propylene glycol acetal, QUINCESTER, MUSK AMBRETTE, FENCHYL ACETATE, Para Cresyl Phenyl Acetate, beta-Terpinyl acetate, DIHYDROCITRONELLAL, Octanal,3,7-dimethyl-, Hexyl trans-2-butenoate, METHYL-2-NONENOATE, DIHYDRO BETA IONONE, Cressanther, n-BUTYL SALICYLATE, NEROLIN BROMELIA, PINO ACETALDEHYDE, ALPHA-BISABOLOL, 10-undecenenitrile, octanal propylene glycol acetal, Terpinyl Methyl Ether, APHERMATE, Irisnitrile, PHENYL ETHYL TIGLATE, Ethyl Caprylate, GLYCOLIERRAL, 1,8-Thiocineol, Lavandulyl acetate, TRIFONE DIPG, beta-Ionone, IONONE BETA, ALPHA DAMASCONE, alpha-damascone, gamma_methyl_ionone, Hexyl neopentanoate, Octyl acetate, Furfuryl heptanoate, BOURGEONAL, AZURIL, IONONE ALPHA, Fleursandol, Khusinil, MACEAL, Pharaone, Oxybenzone, O-Methyl linalool, Floralozone, FLORALOZONE, Andrane, GERANYL ACETATE, NERYL ACETATE, 3-Thujopsanone, TERPINYL ACETATE, 4,5,6,7-Tetrahydro-3,6-dimethylbenzofuran, Methyl Diphenyl Ether, MELAFLEUR, alpha-Phellandrene, Phenethyl 2-methylbutyrate, DAMASCENONE TOTAL, Damascenone,trans-, LEMONILE, LINALYL ACETATE, BETA PINENE, Phenyl Ethyl Benzoate, Trichloromethyl Phenyl Carbinyl Acetate, CAMPHENE, Ethyl 3,7-dimethyl-2,6-octadienoate, ISO BORNYL PROPIONATE, 2-Decene-1-al, Calyxol (Quest), TRANS-2-DECENAL, PIVACYCLENE, DIHYDRO ALPHA IONONE, Menthyl formate, SABINENE, Ambrinol 20T, EBANOL, DUPICAL, FLEURAMONE, Gyrane, Prenyl Salicylate, UNDECAVERTOL, UNDECYLENIC ALDEHYDE, Benzyl phenylacetate, AMBRINOL, Tetrahydroionol, DAMASCONE BETA, Silvial®, VELOUTONE, 4,7-Methano-1H-inden-6-ol, 3a,4,5,6,7,7ahexahydro-8,8-dimethyl-, propanoate, alpha-Fenchene, FLORAL SUPER, GALBASCONE, NONYL ALCOHOL, NEO HIVERNAL, Myrac Aldehyde, Hindinol, HINDINOL, (−)-Carvyl acetate, mixture of cis and trans, Isoamyl salicylate, mixture of isoamyl and 2-methylbutyl salicylates, L-Dihydrocarvyl acetate, mixture of isomers, FRUTONILE, 2-T-BUTYLCYCLOHEXYLOXY-2-BUTANOL, DIPHENYL OXIDE, PERILLA ACETATE, dimethyl cyclohexyl 3-butenyl ketone, POIRENATE, Isodamascone N, ALLO-OCIMENE, ALDEHYDE SUPRA, 2-p-Menthadiene, CAPRIC ACID NAT, DIMETHYL BENZYL CARBINYL BUTYRATE, CASHMERAN, CITRONELLYL ACETATE, Koavone, BENZYL ISO EUGENOL, NOOTKATONE, Butyl sulfide, Hexyl-2-Methyl Butyrate, MUSK RI, DIPHENYL METHANE, PHENYL ETHYL PHENYL ACETATE, BENZYL SALICYLATE, NOPYL ACETATE, Alicate, CINNAMYL CINNAMATE NAT, CIS-3-HEXENYL CIS-3-HEXENOATE, Gamma Terpinene, 12 OXAHEXADECECANOLIDE, CYCLOHEXYL SALICYLATE, MUSK KETONE, Phenyl Ethyl Isoamyl Ether, Apritone, IRONE ALPHA REFINED, PARA CYMENE, FLEURANIL, ETHYL 2,4-DECADIENOATE, (+)-alpha-pinene, ALPHA PINENE, L-ALPHA PINENE, Methyl diphenyl ether, Brahmanol, Spirambrene, CIS-3-HEXENYL BENZOATE, alpha-Methyl Ionone, b-METHYL IONONE, Herbavert, cis-Pinane, METHYL NONYL KETONE, AMYL BENZOATE, Rholiate, Mefloral, P.T.BUCINAL, Wolfwood, Geranyl Propionate, GIVESCONE, ALLYL CYCLOHEXANE PROPIONATE, PEONILE, NECTARYL, LINALYL PROPIONATE, Terpinyl propionate, AMYL SALICYLATE, beta-isomethyl ionone, BORONAL, OXALIDE T, HEXYL TIGLATE, 3-Carene, AURANTIOL, IONONE, GAMMA METHYL, Datilat, DECYL ALDEHYDE, PHENAFLEUR, alpha-Sinensal, Ethyl nonanoate, 7-Methyloctyl acetate, ABIERATE CN, Isobornyl isobutyrate, (E)-β-Ocimene, cis Ocimene, OCIMENE, Neocaspirene Extra, METHYL OCTYL ACETALDEHYDE, SPIROGALBANONE, Nirvanol, POLYSANTOL 2-Heptyl tetrahydrofuran, VELTONAL, ETASPIRENE, 2-nonanone propylene glycol acetal, Citryl acetate, GRISALVA, Belambre, CIS-3-HEXENYL SALICYLATE, Vetikol Acetate, Pinyl Iso Butyrate Alpha, 2-Undecene-1-al, Rhodalione, Citronellyl ethyl ether, alpha-Vetivone, Spathulenol, Citrathal, MYRCENE, Citronellyl Propionate, JAVANOL, LAEVO TRISANDOL, Elintaal Forte, TERPINEOLENE, OCTALYNOL, alpha-Terpinene, THESARON, Nebulone, Theaspirane, mixture of cis and trans, I-Limonene Natural, ORANGE OIL COLD PRESSED, ORANGE TERPENES, PRECYCLEMONE B, Precyclemone B, LINALYL ISO BUTYRATE, BIGARADE OXIDE, p-Cresyl n-hexanoate, FURFURYL OCTANOATE, Rosamusk, Elemol, ISO BORNYL CYCLOHEXANOL SINENSAL, NATURAL, MIXTURE OF ALPHA & BETA, 4-TERTIARY BUTYL CYCLOHEXYL ACETATE, Menthanyl Acetate, VERDOX, Verdox HC, Vertenex, HEALINGWOOD, GERANYL ISOBUTYRATE, NERYL ISOBUTYRATE, α-Amylcinnamyl alcohol, mixture with Amyl hydrocinnamyl alcohol, SANDALORE, ETHYL-2-TERT-BUTYLCYCLOHEXYL CARBONATE, Linalyl butyrate, Mandaril, CEDROL, (+)-D-Menthyl acetate, Isomenthyl acetate, MENTHYL ACETATE, Salviac, Myraldyl acetate, beta-Vetivone, INDOLENE, Cetonal, Ysamber K, YSAMBER K, Dibenzyl, Caryolan-ol, Geranyl Butyrate, Dihydro Ambrate, Amyl Cinnamate, Tetrahydro Geranyl Acetate, Guaiol, AMYL CINNAMIC ALDEHYDE, beta-santalol, Hexyl hexanoate, beta-Himachalene oxide, ROMANDOLIDE, Palisandal, 3,6-Dimethyl-3-octanyl acetate, TETRAHYDRO LINALYL ACETATE, UNDECYL ALDEHYDE, Myrrhone, 3-Bisabolol, ONCIDAL, Bulnesol, I-Citronellyl Isobutyrate, Nonyl Acetate, Ethyl Undecylenate, HEXALON, Cassiffix, Cassiffix, LAURIC ACID (NATURAL), Dibutyl_o-phthalate, tau-Cadinol, A-cadinol, T-Muurolol, I-Citronellyl n-Butyrate, OXYOCTALINE FORMATE, alpha-Agarofuran, (e,e)-FARNESOL, FARNESOL, ISO E SUPER OR WOOD, Boisiris®, Viridiflorol, OCTYL-2-FUROATE, MUSK TIBETENE, NEROLIDOL, HABANOLIDE, GERANYL TIGLATE, Hexyl benzoate, FIF/UL Mandarinal, EXALTENONE, CEDROXYDE®, alpha-santalol, Hydroxymethyl-isolongifolene in dipropylene glycol, 10-epi-gamma-Eudesmol, HEXYL SALICYLATE, γ-Eudesmol, PHENYL ACETALDEHYDE DIMETHYL ACETAL, GALBANOLENE SUPER, Ambrocenide, (Z)-4-dodecen-1-al, NORLIMBANOL, ACALEA TBHQ, geranyl valerate, HEXYL CINNAMIC ALDEHYDE, AGRUMEA, Agrumea, isoamyl octanoate, (E)-5-Tangerinol, (Z)-5-Tangerinol, (Z)-3-Dodecenal, Kusunol, Undecene 2 Nitrile, 7-epi-alpha-Eudesmol, alpha-Eudesmol, CEDRYL FORMATE, METHYL CEDRYLONE, Operanide, Ozofleur, TRIMOFIX O, Lauryl alcohol, SCLAREOL, METHYL NONYL ACETALDEHYDE, Ethyl Caprate, CYCLOPENTADECANONE, 1,3-Dioxane 2-(2,4-dimethyl-3-cyclohexen-1-yl)-5-methyl-5-(1-methylpropyl)-, I-Citronellyl Tiglate, BUTYLATED HYDROXY TOLUENE, CEDRYL METHYL ETHER, Maritima, 1-Methyl-4-(1-methylethyl)-cyclohexane, p-Menthane, LAURIC ALDEHYDE, AMBRONAT, CETALOX, CLONAL, LINALYL ANTHRANILATE, Palisandin, 2,6,10-Trimethylundecanal, Nirvanolide, 2-TRIDECENAL (HIGH TRANS) FCC, DELTA MUSCENONE, Serenolide®, 5-CYCLOHEXADECEN-1-ONE, Adoxal, Amberketal IPM, SANTALEX T, BOISAMBRENE FORTE, EXALTOLIDE TOTAL, Parsol MCX, alpha-Curcumene, Curzerene, vetiveryl acetate, HELVETOLIDE, 1,1,2,3,3-Pentamethylindan, Phantolid Crystals, β-Selinene, METHYL NONYL ACETALDEHYDE DIMETHYL ACETA, Decanal diethyl acetal, CEDAC, Celestolide, alpha-Cubebene, ALPHA-AMYLCINNAMYL ACETATE, Dodecanal dimethyl acetal, CYCLOHEXADECENONE, N-Decyl Propionate, LINALYL BENZOATE, HYDROXYAMBRAN, Citronellyl benzoate, geranyl phenyl acetate, GERANYL PHENYLACETATE, beta-Patchoulline, 2-TRIDECENENITRILE, ALPHA-FARNESENE, CARYOPHYLLENE ACETATE, FARNESYL ACETATE, GERANYL BENZOATE FCC, Acetoxymethyl-isolongifolene (isomers), alpha-bisabolene, Trisamber®, delta-Elemene, Cis-Iso-Ambrettolide, Oxacycloheptadec-8-en-2-one, trans-Ambrettolide, SILVANONE CI, AMBRETTOLIDE, LAEVO MUSCONE, beta-Guaiene, I-Citronellyl Phenylacetate, beta-Sesquiphellandrene, Butyl Undecylenate, Amyl Cinnamic Aldehyde Diethyl Acetal, Iso Amyl Undecylenate, Germacrene D, Amber xtreme—Compound 2, beta-Cedrene, gamma-Gurjunene, GERANYL CAPROATE, Civettone, OKOUMAL, ethyl laurate, (–)-β-Himachalene, BISABOLENE, Lauryl acetate, alpha-Santalene, Decane, Valencene, TRIDECYL ALCOHOL, BRANCHED, 7-epi-Sesquithujene, Sclareol oxide, Vulcanolide, Selina-3,7(11)-diene, alpha-Patchoulene, TRANS-BETA-FARNESENE, CITRONELLYL CAPROATE, β-Copaene, delta-Guaiene, 7-epi-alpha-Selinene, HEXAMETHYLINDANOPYRAN, α-Selinene, Allo-aromadendrene, ISOPROPYL LAURATE, Thujopsene, β-Cadinene, γ-Muurolene, Germacrene B, A-CARYOPHYLLENE, Amber Xtreme, alpha-Amorphene, alpha-Muurolene_2, α-Cadinene, Hexyl octanoate, γ-Himachelene, α-Bergamotene, ALDEHYDE C-14 MYRISTIC, Indolene, α-Gurjunene, Decyl anthranilate, Myristo nitrile, P.T. BUCINAL METHYL ANTHRANILATE, CARYOPHYLLENE EXTRA, HEXAHYDROFARNESYL ACETONE, alpha-Himachalene, Geranyl linalool (all trans), Cyclotetradecane, Methyl myristate, Isoamyl laurate, I-Hexadecanol, GERANYL CAPRYLATE, LINALYL OCTANOATE, METHYL LINOLEATE, Ethyl myristate, BENZYL LAURATE, Methyl Palmitate, ETHYL PALMITATE, ISOPROPYL PALMITATE NF, Methyl stearate, Butyl stearate, HEXAROSE, and mixtures of two, three, four or more thereof, preferably isopropylmyristate, galaxolide, habanolide, Operanide, Okoumal Silkolide, Musk Plus, Helvetolide, Romandolide, Celestolide or a mixture of two, or three, or four or more thereof.

It can be preferred if the first malodor suppressant is selected from the group consisting of isopropylmyristate, galaxolide, habanolide or mixtures of isopropylmyristate and galaxolide or isopropylmyristate and habanolide or galaxolide and habanolide.

It can further be preferred if the second malodor suppressant is selected from the group consisting of isopropylmyristate, galaxolide, habanolide or mixtures of isopropylmyristate and galaxolide or isopropylmyristate and habanolide or galaxolide and habanolide.

It has often proven to be successful if the first and the second malodor suppressant are, e.g., isopropylmyristate and habanolide, or isopropylmyristate and galaxolide.

In a further rembidement of the invention the first and second malodor suppressants are a liquid at 23° C. and 1013 mbar In a still further embodiment of the invention in a combination of first and second malodor suppressants at least two malodor suppressants have a log P of 3 or more and a molecular weight of 100-400.

Generally the malodor suppressant can be present in any of the components (i) or (ii) or in both components, it has, however, proven in some cases to be advantageous if the malodor suppressant is present in at least the component which comprises a gel-network as defined above, preferably at least in the component comprising the ammonia compound or two or more ammonia compounds.

In a hair colouring and/or bleaching composition according to the invention the malodor suppressant or the combination of first and second malodor suppressants can be present in the first composition (i) in an amount of 0 to 70% by weight, and the combined amount of malodor suppressant in the first and second composition is at least 0.01% by weight, or the combination of malodor suppressants is present in the first composition (i) in an amount of 0 to 40% by weight, and the combined amount of malodor suppressant in the first and second composition is at least 0.1% by weight.

In a hair colouring and/or bleaching composition according to the invention the malodor suppressant can be present in the second composition (ii) in an amount of 0 to 70% by weight, and the combined amount of malodor suppressant in the first and second composition is at least 0.01% by weight, or the combination of malodor suppressants is present in the second composition (li) in an amount of 0 to 40% by weight, and the combined amount of malodor suppressants in the first and second composition is at least 0.1% by weight.

The viscosity of a hair coloring and/or bleaching composition according to the invention, the composition should, after mixing, have a viscosity which enables an adaption to generally all useful ways of applying the composition to the hair. This can be, e.g., a very fluid state of matter which enables a rapid application, but can also be a more viscous state, which allows for a longer residence time on the hair also under vertical conditions. Thus, it can be preferred if the hair coloring and/or bleaching composition according to the invention after mixing of compositions (i) and (ii), has a viscosity of from 200 to 2000 cPs, e.g., from 300 to 1500 cPs or from 400 to 1000 cPs. Viscosity is measured using Brookfield viscometers with cone and plate attachment. For viscosities in the range of 0 to 12000 cPs, the Brookfield DV-11 viscometer with S42 plate is used. 2 ml sample of the composition is equilibrated at 26.7° C. for three minutes before the readings are taken at 1 rpm.

The hair coloring and/or bleaching composition can further comprise fatty compound(s) selected from the group consisting of mineral oil, hydrocarbon oil, and mixtures thereof in an amount of up to 30%, by total weight of the composition, e.g., in an amount of 10.1 to 28% or 1.5 to 25% or 1 to 15% or 3 to 10% by weight. Commercially suitable raw materials include materials of the Marcol™ Series from ExxonMobile, particularly Marcol™ 52 and Marcol™ 82.

The composition comprises a cosmetically acceptable carrier or solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglycol, polyglycerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least 50%, alternatively from at least 60%, alternatively from at least 70%, by total weight of the composition. Typically, when present, the composition comprises a total amount of organic solvents ranging from 1% to 30%, by total weight of the composition.

The composition may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof. The oxidative dye precursors are generally present in hair treatment compositions which are hair colorants and usually are part of the composition called "tint", i.e., in the present case in component (ii).

Typically, the composition may comprise a total amount of oxidative dye precursors ranging up to 12%, alternatively from 0.1% to 10%, alternatively from 0.3% to 8%, alternatively from 0.5% to 6%, by total weight of the composition, preferably all comprised in a single component, in the present case preferably component (ii).

Suitable primary intermediates, which are also generally present in hair treatment compositions which are hair colorants, include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-methylenebis-4-aminophenol, 2,4,56-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydromethyl)-N-(4-aminophenyl)-1,2-diaminothane, salts thereof and mixtures thereof. The primary intermediates are also preferably present in the component called "tint", i.e., in component (ii) in the present case.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6- chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof. The couplers are also preferably present in the component called "tint", i.e., in component (ii) in the present case.

The composition may further comprise compatible direct dyes, in an amount sufficient to provide additional coloring, particularly with regard to intensity. Typically, the composition may comprise a total amount of direct dyes ranging from 0.05% to 4%, by total weight of the composition.

Suitable direct dyes include but are not limited to: Acid dyes such as Acid Yellow 1, Acid Orange 3, Acid Black 1, Acid Black 52, Acid Orange 7. Acid Red 33. Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26. Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol. HC Blue No. 12, HC Yellow No, 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No, 14; Natural dyes such as Annato, Anthocyanin, Beetroot, Carotene, Capsanthin, Lycopene, Chlorophyll, Henna, Indigo, Cochineal; and mixtures thereof. The direct dyes are also preferably present in the component called "tint", i.e., in component (ii) in the present case.

The composition may further comprise one or more chelant(s) (also known as "chelating agent", "sequestering agent", or "sequestrant") in an amount sufficient to reduce the amount of metals available to interact with formulation components, particularly oxidizing agents, more particularly peroxides. Any suitable chelant known in the art may be used.

The composition may comprise a total amount of chelant(s) ranging from at least 0.01%, alternatively from 0.01% to 5%, alternatively from 0.25% to 3%, alternatively from 0.5% to 1%, by total weight of the composition.

Suitable chelant(s) include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

The composition may comprise chelant(s) selected from the group consisting of diethylenetriamine-N,N',N'''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

The composition may further comprise one or more radical scavenger(s). As used herein the term "radical scavenger" refers to a species that can react with a radical, preferably a carbonate radical to convert the radical species by a series of fast reactions to a less reactive species. In one embodiment, the radical scavenger(s) is different from the alkalising agent and/or is present in an amount sufficient to reduce the damage to the hair during the colouring/bleaching process.

The composition may comprise a total amount of radical scavenger(s) ranging from 0.1% to 10%, alternatively from 1% by weight to 7%, by total weight of the composition.

Suitable radical scavenger(s) includes, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperidine, ethylamine, 3 amino-1-propanol, and mixtures thereof. As used herein, the term "salts thereof"—in the context of radical scavengers—means particularly potassium salts, sodium salts, ammonium salts, and mixtures thereof.

The composition may further have a pH of from 3 to 13, alternatively from 8 to 12, alternatively from 9 to 11. The composition may also comprise, in addition to the alkalizing agent(s) discussed above, pH modifier(s) and/or buffering agent(s) in an amount that is sufficiently effective to adjust the pH of the composition to fall within a range from 3 to 13, alternatively from 8 to 12, alternatively from 9 to 1.

Suitable pH modifier(s) and/or buffering agent(s) include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3-propandiol); guanidium salts; alkali metal and ammonium hydroxides and carbonates; and mixtures thereof.

Further pH modifier(s) and/or buffering agent(s) include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

The composition may further comprise thickener(s) and/or rheology modifier(s) in an amount sufficient to provide the composition with a viscosity so that it can be readily applied to the hair without unduly dripping off the hair and causing mess.

The composition may comprise a total amount of thickener(s) ranging from at least 0.1%, alternatively at least 0.5%, alternatively at least 1%, by total weight of the composition.

Suitable thickener(s) include, but are not limited to: associative polymers, polysaccharides, non-associative polycarboxylic polymers, and mixtures thereof. Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrrollidone (Povidone), Acrylates/Ceteth-20 Itaconate Copolymer (Structure 3001), hydroxypropyl starch phosphate (Structure ZEA), polyethoxylated urethanes or poly carbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth-10 phosphate, Di-cetyl phosphate and Cetearyl alcohol (available as Crodafos CES), and mixtures thereof. The composition may comprise a total amount of thickener(s) selected from anionic and cationic polymer(s) of less than 1%, alternatively less than 0.1% by total weight of the composition.

The composition may further comprise a source of carbonate ions, carbamate ions, hydrogen carbonate ions, and mixtures thereof in a sufficient amount to reduce damage to the hair during the coloring process.

The composition may comprise a total amount of a carbonate ion source ranging from 0.1% to 15%, alternatively from 0.1% to 10%, alternatively from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammoniun hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

The composition may further comprise one or more conditioning agent(s), and/or be used in combination with a composition comprising one or more conditioning agent(s). Any suitable conditioning agent(s) known in the art may be used.

The composition may comprise a total amount of conditioning agent(s) ranging from 0.05% to 20%, alternatively from 0.1% to 15%, alternatively from 0.2% to 10%, alternatively from 0.2% to 2%, alternatively from 0.5% to 2%, by total weight of the composition. The conditioning agent(s) may be included in a separate pre- and/or post-treatment composition.

Suitable conditioning agent(s) include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agent(s) include mineral oils and other oils such as glycerin and sorbitol. The composition may comprise a total amount of cationic conditioning agent(s) of less than 1%, alternatively less than 0.1% by total weight of the composition.

The composition may further comprise surfactant(s), other than the non-ionic surfactant(s). Suitable surfactant(s) generally have a lipophilic chain length of from 8 to 30 carbon atoms and can be selected from anionic surfactants, amphoteric surfactants, cationic surfactants, and mixtures thereof. Any suitable surfactant(s) known in the art may be used.

The composition generally comprises a total amount of anionic surfactant(s) of less than 2%, alternatively less than 1%, alternatively less than 0.5% by total weight of the composition. Alternatively, the composition may be free of anionic surfactant(s).

The composition comprises a total amount of cationic surfactant(s) of less than 2%, alternatively less than 1%, alternatively less than 0.5% by total weight of the composition. Alternatively, the composition may be free of cationic surfactant(s).

The composition may be free of anionic surfactant(s) and free of cationic surfactant(s). The inventors have surprisingly found that a greater reduction of ammonia odour is achieved when the hair colouring and/or bleaching composition is free of anionic and/or cationic surfactant(s).

The composition may comprise a total amount of surfactant(s) other than fatty alcohol(s) and non-ionic surfactant(s) of less 1%, alternatively less than 0.5%, alternatively less than 0.3%, alternatively less than 0.1%.

The composition may comprise, in addition to the ingredients indicated above, further ingredients in order to further enhance the properties of the composition, as long as these are not excluded by the claims. Suitable further ingredients include, but not limited to: solvents; peroxymonocarbonate ion sources; anionic, cationic, nonionic, amphoteric or zwitterionic polymers, and mixtures thereof; fragrances; enzymes dispersing agents; peroxide stabilizing agents; antioxidants; natural ingredients (such as proteins, protein compounds, and plant extracts); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

The composition may be free of amine compounds and/or phospholipid compounds; alternatively may be free of fatty monoamine compounds, polyamine compounds having at least three amino groups and fatty quaternary amine compounds and/or phospholipid compounds.

The composition may comprise a total amount of polymer(s) selected from anionic and cationic polymer(s) of less than 1%, alternatively less than 0.1% by total weight of the composition. Alternatively, the composition may be free of anionic and cationic polymer(s).

The oxidizing agent(s), the alkalizing agent, the fatty alcohol(s), the non-ionic surfactant(s), the fatty compound(s) and the cosmetically acceptable carrier, to be incorporated into the first and/or the second component, have been defined hereinbefore. Likewise, any suitable optional compounds including the oxidative dye precursor(s), the direct dye(s), the chelant(s), the radical scavenger(s), pH modifier(s) and/or buffering agent(s), thickener(s) and/or rheology modifier(s), carbonate ion source(s), conditioning agent(s), surfactant(s), and any further ingredients, to be incorporated into the first and/or the second composition, have also been defined hereinbefore.

The first and the second components may be mixed for 5 sec to 3 min, alternatively for 15 sec to 2 min, alternatively for 30 sec to 1 min.

Depending on stability and reactivity considerations, the compounds may be incorporated indifferently into the first and/or the second components, or may preferably be incorporated into one of the two components. The fatty compound(s) selected from the group consisting of a mineral oil, hydrocarbon oil, and mixtures thereof when present may be incorporated into the first component, the second component being free of said fatty compound. The fatty alcohol(s) and/or the non-ionic surfactant(s) may be incorporated into the first component and/or the second component.

The oxidative dye precursors including the primary intermediates and couplers are usually incorporated into the second component. The direct dyes are usually incorporated into the second component. The chelant may be incorporated into the first and/or the second component, however the chelant is usually incorporated into the first component for stability reason.

The invention further relates to a hair colouring or bleaching kit comprising
An individually packaged first aqueous component (i) comprising, in a cosmetically acceptable carrier one or more oxidizing agent(s) and An individually packaged second aqueous component (ii) comprising in a cosmetically acceptable carrier one or more alkalizing agent(s) selected from the group consisting of ammonia, its salts and mixtures thereof, wherein the first component (i) or the second component (ii) or both components (i) and (ii) comprise a gel-network system consisting of multi-lamellar sheets or vesicles or both, with d-spacing (interlayer spacing between sheets) between 5 nm and 50 nm, preferably 10 nm to 40 nm, more preferred 15 nm to 30 nm as measured by Small Angle X-Ray Scattering (SAXS), and the first component (i) or the second component (ii) or both comprise less than less than 2% of anionic surfactants other than phosphate esters and less than 2% of cationic surfactants and the first component (i) or the second component (ii) or both comprise at least a first malodor suppressant being a compound having a distribution coefficient log P of 2 or more and a molecular weight of between 100 and 400 or a at least first and a second malodor suppressant, both being a compound having a distribution coefficient log P of 2 or more and a molecular weight of between 100 and 400.

The description of components (i) and (ii) above also applies to components (i) and (ii) of the kit. In the hair colouring or bleaching kit according to the invention the malodor suppressant is selected from the group of compounds described above and named "list of malodor suppressants."

Individually packaged components mean that they may be packaged in separate containers or in compartmented containers. The consumer mixes the first component and the second component together immediately before use and applies it onto the hair. The first and the second components may be mixed from 5 sec to 3 min, alternatively from 15 sec to 2 min, alternatively for 30 sec to 1 min prior application to the hair.

After working the combined mixture for a few minutes (to insure uniform application to all of the hair), the hair colouring and/or bleaching composition is allowed to remain on the hair for an amount sufficient for the dyeing to take place, usually from 2 min to 60 min, typically from 30 min to 45 min. The consumer or salon professional then rinses the hair thoroughly with water and/or shampoo and allows it to dry. It will be observed that the hair has changed from its original colour to the desired colour.

The kit may also comprise a third component selected from the group consisting of a conditioning composition, a pre-treatment composition, and/or a colour refresher composition. The pre-treatment may be applied onto hair, before applying the hair colouring and/or bleaching composition. The conditioning composition, comprising a conditioning agent, may be mixed together with the first and the second component prior to application onto hair, or may be alternatively applied separately onto hair, for example after applying the hair colouring and/or bleaching composition. The colour refresher composition, comprising optionally a pre-formed dye, may be applied after applying the hair colouring and/or bleaching composition. The component could be also a carrier for dye precursors or concentrates.

The invention also relates to a method of treating hair comprising the steps of applying a hair colouring or bleaching composition after mixing as described above or a composition obtainable as a mixture from a kit as described above to the hair, leaving said composition on the hair for from 2 to 60 minutes and subsequently rinsing said composition from the hair.

The method of colouring and/or dyeing hair comprises applying onto hair a hair colouring and/or bleaching composition as defined herein before. The method may comprise the steps of: providing a first component as defined hereinbefore; providing a second component as defined hereinbefore; mixing the first and the second components for obtaining a hair colouring and/or bleaching composition; applying the obtained composition onto hair, leaving the applied composition on hair from 5 min to 60 min. alternatively 10 min to 30 min; optionally rinsing hair using a rinsing composition, alternatively rinsing hair with water; optionally cleansing hair using a cleansing composition; optionally treating hair with a conditioning and/or treating composition; and, optionally drying hair.

The compositions in each container of the kit can be nmanufactured utilizing any one of the standard approaches, these include a) 'Oil-in-water' process, b) 'Phase Inversion' process and c) 'One-pot' process. For example, when using "oil-in-water" process, surfactants of the present invention are added to approximately 50% of total water amount of the composition at 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or colouring kit.

The present invention may be provided in a variety of packaging devices and/or dispensing devices. These dispensing devices can come in the form of separate devices which may be used independently or in combination with one another. Typically, the hair colouring and/or bleaching compositions are contained within separate single or multi-compartment containers so that the compositions can be stored separately from one another before use. The compositions are then mixed together by a mixing means and then dispensed from the device and applied to the consumer's hair by an application means.

The most common packaging device which can be used involves storing the developer component in a container such as a bottle, tube, aerosol, or a sachet and separately storing the dye component in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the developer component and the tint component by any means, including by using a mixing bowl and/or a mixing tool, by adding one component into the container of the other component followed by mixing, or by perforating or displacing a seal located between the separate compartments of the components within a single container or sachet followed by mixing.

The devices described herein above can also be used in combination with a product delivery and or application tool to aid application of the product onto the hair, including using a nozzle attached to one of the containers, using a separate applicator device such as a comb or brush, using a comb attached to or instead of the dispensing nozzle whereby the product is dispensed through hollow tines and dispensing apertures located in the comb tines. The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used. Additional device technology can be used to assist in the penetration of the product into the hair. Examples of such technology include heating devices, ultraviolet light devices and ultrasound devices. The hair colouring and/or bleaching composition, and the corresponding first and second components, may be manufactured by conventional processes known in the art for manufacturing oxidative hair colouring and/or bleaching products, and ad-mixing the ingredients of each component composition in suitable vessels, followed by packaging in appropriate individual containers.

The invention further relates to a method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition as described above or obtainable as a mixture from a kit as described above, applying said composition to the hair and retaining said composition on the hair for a time period of less than 40 minutes and subsequently rinsing said composition from the hair.

In another aspect, the invention relates to the use of a hair colouring and/or bleaching composition according to any of claims 1 to 12 or of a kit according claim 13 for colouring and/or bleaching hair with a reduced or eliminated ammonia odour.

The invention will further be described by the following experimental data.

Experimental

SAXS and WAXS measurements were simultaneously carried out on a Xenocs Xeuss 2.0 instrument with the following specifications and settings:
Instrument working condition: 50 kV/0.6 mA
Incident X-ray beam wave length: 1.5419 nm
Beam size: 0.8 mm×0.8 mm
Sample-to-detector distance for SAXS: 1196 mm
Scan per sample: 60 minutes The hair color or bleach composition was inserted into XRD quartz capillaries of 2 mm diameters and 80 mm lengths and then placed into a sample holder which is located between the X-Ray source and the SAXS/WAXS detectors.

In order to determine the influence of the malodor suppressants on different ammonia containing systems, test samples were provided and analyzed. Samples 1 and 2 were simple 25% solutions of ammonia in water. Gel-Network (GN) and Non-Gel-Network (NGN) samples were prepared as follows:
GN Tint:

| Raw Materials | |
|---|---|
| Crodafos ® CES (Cetearyl alcohol, di-cetyl phosphate & ceteth-10 phosphate) | 5 |
| Cetearyl alcohol | 1.65 |
| Steareth-200 | 0.5 |
| Ammonia (25%) | 4.095 |
| Propylene glycol | 3 |
| Xanthan Gum | 0.04 |
| EDTA (tetrasodium salt) | 0.05 |
| Ascorbic Acid | 0.2 |
| Sodium sufite | 0.05 |
| Sodium sulfate | 0.5 |
| EDDS (trisodium salt) | 1 |
| Sodium lauryl sulfate | 0.1 |

-continued

| Raw Materials | |
|---|---|
| NH3 suppression components | 0.7 |
| Water qs | 83.115 |

NGN Tint:

| Raw Materials | % weight |
|---|---|
| Cetaryl Alcohol | 9.5 |
| Glyceryl Stearate SE | 8 |
| Glyceryl oleate | 2 |
| Ceteareth-25 | 2 |
| EDTA disodium salt | 0.05 |
| Etidronic Acid | 0.05 |
| Sodium Sulfite | 0.05 |
| Ascorbic acid | 0.2 |
| Sodium sulfate | 0.5 |
| Ammonia solution (25%) | 4.095 |
| NH3 suppression components | 0.7 |
| Sodium Lauryl Sulfate 70% | 4 |
| Water qs | 68.855 |

The developer consists of the following raw material composition:
Welloxon 9%

| Raw Materials | |
|---|---|
| Cetearyl alcohol | 3.4 |
| Ceteareth-25 | 0.8 |
| Etidronic acid, 85% | 0.01 |
| Phosphoric acid, 85% | 0.1 |
| Salicylic acid | 0.1 |
| Disodium phosphate | 0.08 |
| Hydrogen peroxide (50%) | 18 |
| Water qs | 77.51 |

Welloxon 6%

| Raw Materials | |
|---|---|
| Cetearyl alcohol | 3.4 |
| Ceteareth-25 | 0.8 |
| Etidronic acid, 85% | 0.01 |
| Phosphoric acid, 85% | 0.1 |
| Salicylic acid | 0.1 |
| Disodium phosphate | 0.08 |
| Hydrogen peroxide (50%) | 12 |
| Water qs | 83.51 |

The wax components of the tint and developer examples are melted to 90° C. The melted wax mixture is then mixed with 90° C. pre-heated water and continuously stirred for 40 minutes. The resulting mixture is then allowed to cool down at a rate of 2° C./min to room temperature and continuous stirring. In case of the GN mixture a gel-network system starts to form, consisting of multi-lamellar sheets and vesicles with a d-spacing (interlayer spacing between sheets) of 25.5 nm as measured by Small Angle X-Ray Scattering (SAXS).

When mixture cools down to 40° C. ammonia, perfume, perfume components for NH3 suppression, and the other non-wax components of the ingredients list are added to the creme under continuous stirring till creme cools down to room temperature (25° C.). The resulting creme is then either packed in aluminum tubes for tint or in PE bottles for developer and the Gel-Network is allowed to form for a minimum of 24 hours.

The total ammonia content of the following samples was analyzed (Table 1) by means of Kjeldahl analysis (GCAS: 58084429):

TABLE 1

| | Samples | |
|---|---|---|
| Sample type | Sample Number | Total Ammonia content % |
| 9.2% ammonia solution (25%) | 1 | 2.41 |
| 9.2% ammonia solution (25%) with 0.7% Galaxolide/IPM | 2 | 2.15 |
| GN without Galaxolide/IPM | 3 | 2.41 |
| NGN with 0.7% Galaxolide/IPM | 4 | 2.52 |
| GN with 0.7% IPM | 5 | 2.09 |
| GN with 0.7% Galaxolide | 6 | 2.14 |
| NGN without Galaxolide/IPM | 7 | 1.61 |
| NGN with IPM/ Galaxolide | 8 | 1.91 |
| NGN with 0.7% IPM | 9 | 1.65 |
| NGN with 0.7% Galaxolide | 10 | 1.95 |

Method

For Samples 1 and 2, 7.5 g of the ammonia solution are mixed with 7.5 g of water. For samples 3 to 10, 7.5 g sample and a developer (Welloxon Perfect 6%) are mixed in an open bowl with a brush until homogeneous. The time until homogeneity was reached was taken for the first GN sample and for the first NGN sample and all following GN and NGN samples were mixed for the time taken for the respective first sample of the GN or NGN type. The obtained mixture is then transferred manually into a 1 l 3-neck round vessel with a KPG-stirrer which is then sealed. The headspace above the mixture is then continuously driven through a gas cell by constant introduction of ambient air into the vessel, and analyzed by means of FTIR (with background correction for ambient air). A kinetic profile is recorded using the absorption bands of ammonia at 926 cm-1 and 966 cm-1 for 1000 seconds. In addition, the total ammonia is absorbed in a boric acid solution in order to quantify the total release by acidimetric titration.

The developer consists of the following raw material composition:
Welloxon 9

| Raw Materials | |
|---|---|
| Cetearyl alcohol | 3.4 |
| Ceteareth-25 | 0.8 |
| Etidronic acid, 85% | 0.01 |
| Phosphoric acid, 85% | 0.1 |
| Salicylic acid | 0.1 |
| Disodium phosphate | 0.08 |
| Hydrogen peroxide (50%) | 18 |
| Water qs | 77.51 |

Welloxon 9

| Raw Materials | |
|---|---|
| Cetearyl alcohol | 3.4 |
| Ceteareth-25 | 0.8 |
| Etidronic acid, 85% | 0.01 |
| Phosphoric acid, 85% | 0.1 |
| Salicylic acid | 0.1 |
| Disodium phosphate | 0.08 |
| Hydrogen peroxide (50%) | 12 |
| Water qs | 83.51 |

Experiments

The following samples were analyzed:

1.
NH3 solution of sample 1 without stirring
NH3 solution of sample 1 with stirring 2.
0.7% Galaxolide/IPM mixture in NH3 solution of sample 2 without stirring
0.7% Galaxolide/IPM mixture in NH3 solution of sample 2 with stirring 3.
0% Galaxolide/IPM in GN (sample 3) without stirring in the vessel, initial mixing time 20 sec
0% Galaxolide/IPM in GN (sample 3) with stirring in the vessel, initial mixing time 20 sec 4.
0.7% Galaxolide/IPM in GN (sample 4) without stirring in the vessel, initial mixing time of tint and developer: 20 sec
0.7% Galaxolide/IPM in GN (sample 4) with stirring in the vessel, initial mixing time of tint and developer: 20 sec 5.
0.7% IPM in GN (sample 5) without stirring in the vessel, initial mixing time of tint and developer: 20 sec
0.7% IPM in GN (sample 5) with stirring in the vessel, initial mixing time of tint and developer: 20 sec 6.
0.7% Galoxolide in GN (sample 6) without stirring in the vessel, initial mixing time of tint and developer: 20 sec
0.7% Galoxolide in GN (sample 6) with stirring in the vessel, initial mixing time of tint and developer: 20 sec.

7.
NGN without Galoxolide/IPM (sample 7) without stirring in the vessel, initial mixing time of tint and developer: 40 sec. Not 20 sec because of the viscosity of the NGN chassis.
NGN with Galaxolide/IPM (sample 8) without stirring in the vessel, initial mixing time of tint and developer: 40 sec.
NGN with 0.7% IPM without stirring in the vessel, initial mixing time of tint and developer: 40 sec.
NGN with 0.7% Galaxolide without stirring in the vessel, initial mixing time of tint and developer: 40 sec.

8.
NGN without Galoxolide/IPM with stirring in the vessel, initial mixing time of tint and developer: 40 sec. Not 20 sec because of the viscosity of the NGN chassis.
NGN with Galaxolide/IPM with stirring in the vessel, initial mixing time of tint and developer: 40 sec.
NGN with 0.7% IPM with stirring in the vessel, initial mixing time of tint and developer: 40 sec.
NGN with 0.7% Galaxolide with stirring in the vessel, initial mixing time of tint and developer: 40 sec.

Experiment 1 and 2: 7.5 g solution is diluted with 7.5 g water, respectively.

Experiment 3, 4, 5 and 6: 7.5 g tint is mixed with 7.5 g Welloxon Perfect 6%, respectively.

Experiment 7/8: 7.5 g tint is mixed with 7.5 g Welloxon Perfect 6%, respectively.

Figure 2:
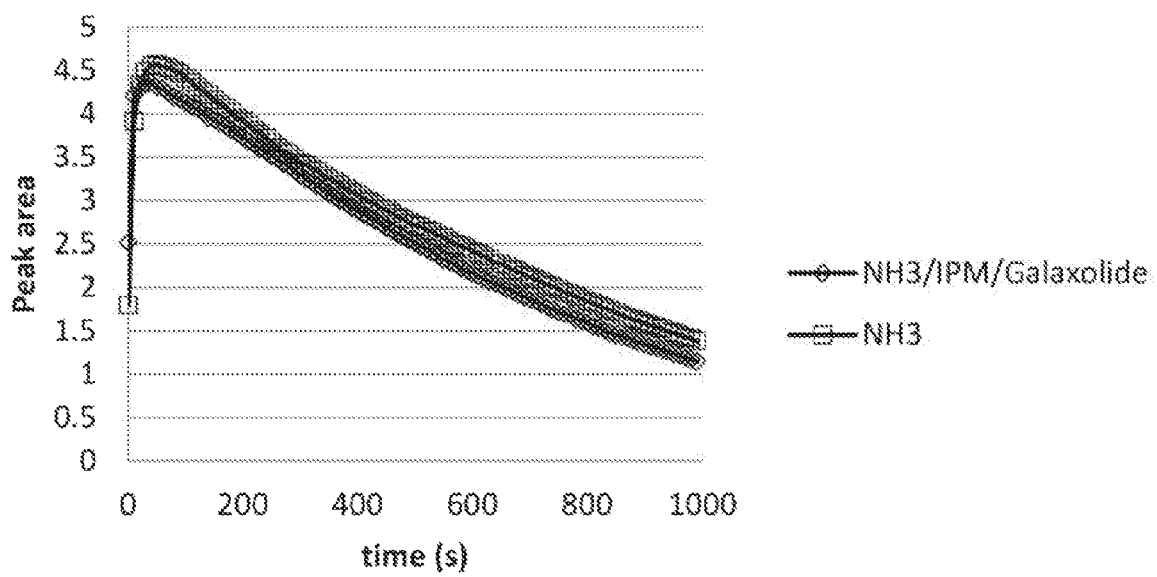
FIG. 2 shows the behavior of the ammonia release kinetic with stirring. No significant differences are observable, which supports the assumption of a physical effect in FIG. 1.
Figure 3:
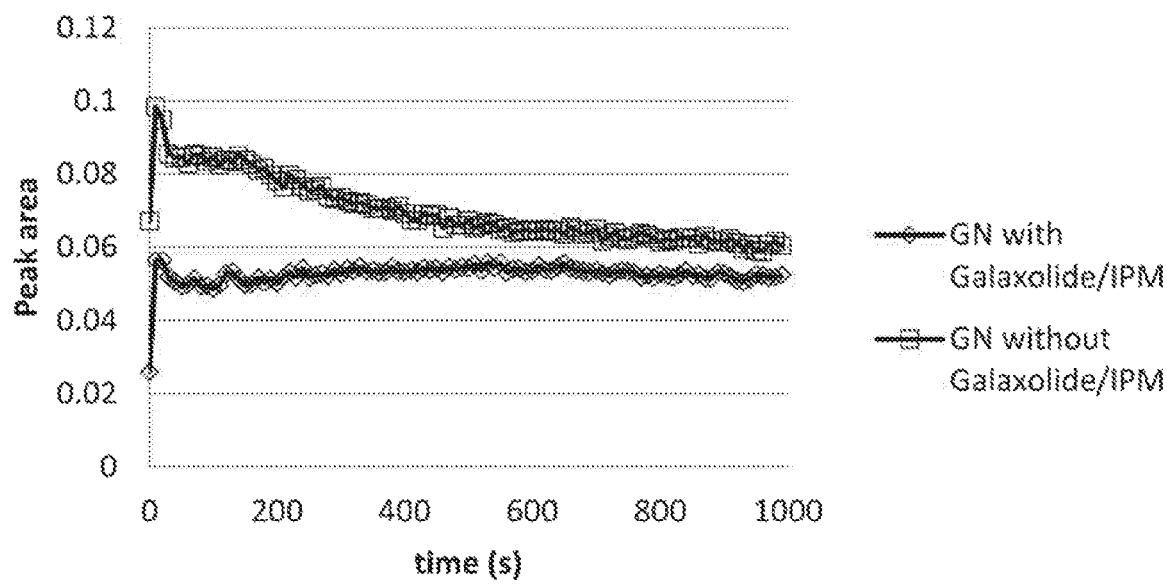
FIG. 3 shows the ammonia release kinetic of GN (tint) with Welloxon 6% without stirring (Examples 3 and 4).
Figure 4:
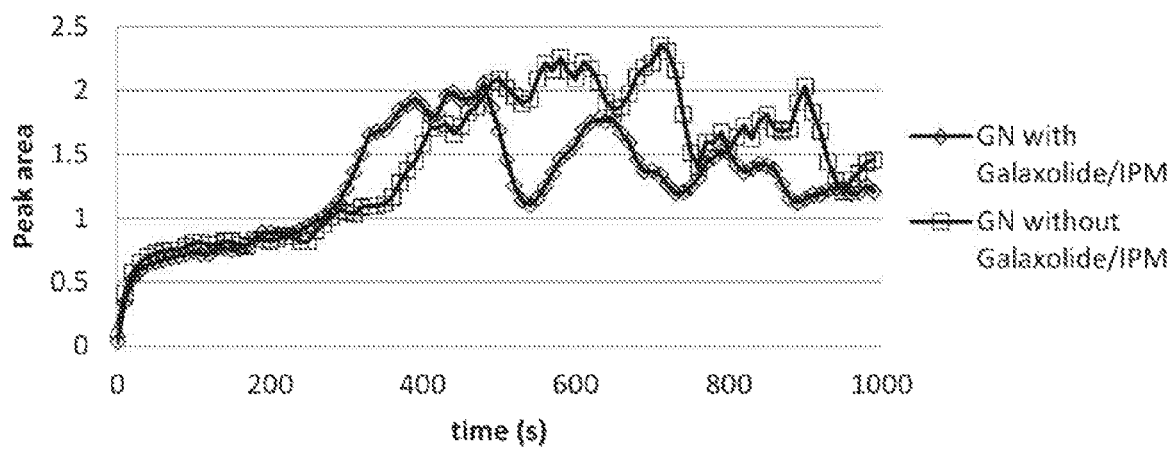
FIG. 4 shows the ammonia release kinetic of GN with Welloxon 6% with stirring (Examples 5 and 6). The curve GN without Galaxolide/IPM is above the curve GN with Galaxolide/IPM. That means that more ammonia is released from the mixture without Galaxolide/IPM.
Figure 5:
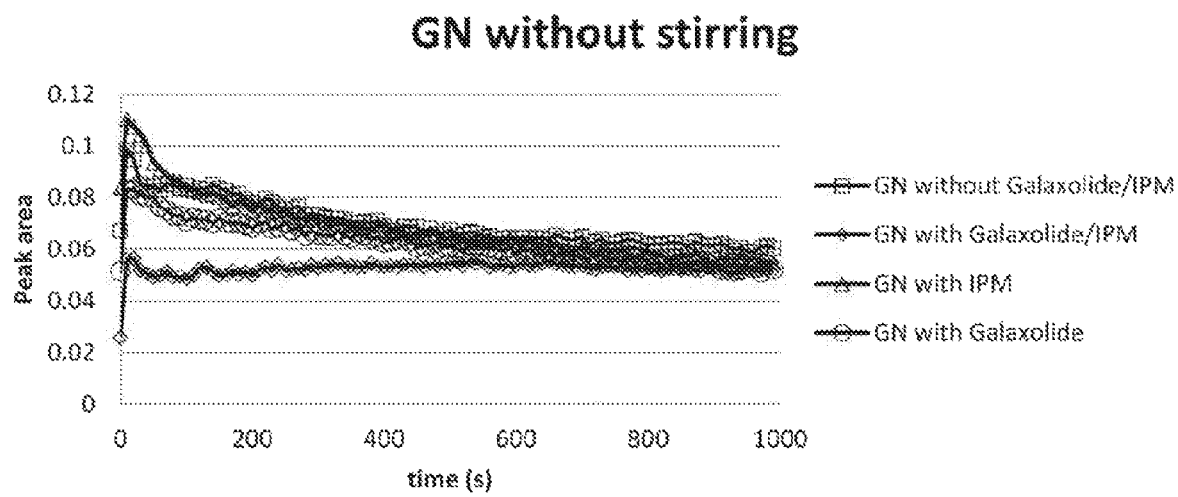
FIG. 5 shows the ammonia release kinetic of GN (tint) with Welloxon 6% (Experiments 3 to 6) without stirring.
Figure 6:
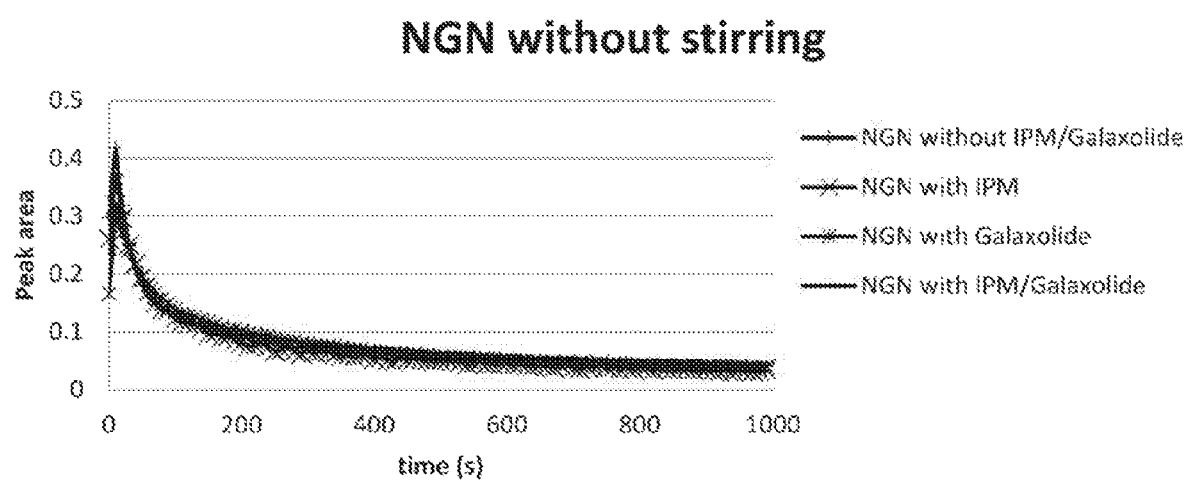
FIG. 6 shows the ammonia release kinetic of NON (tint) with Welloxon 6% (Experiments 7 and 8) without stirring.
Figure 7:
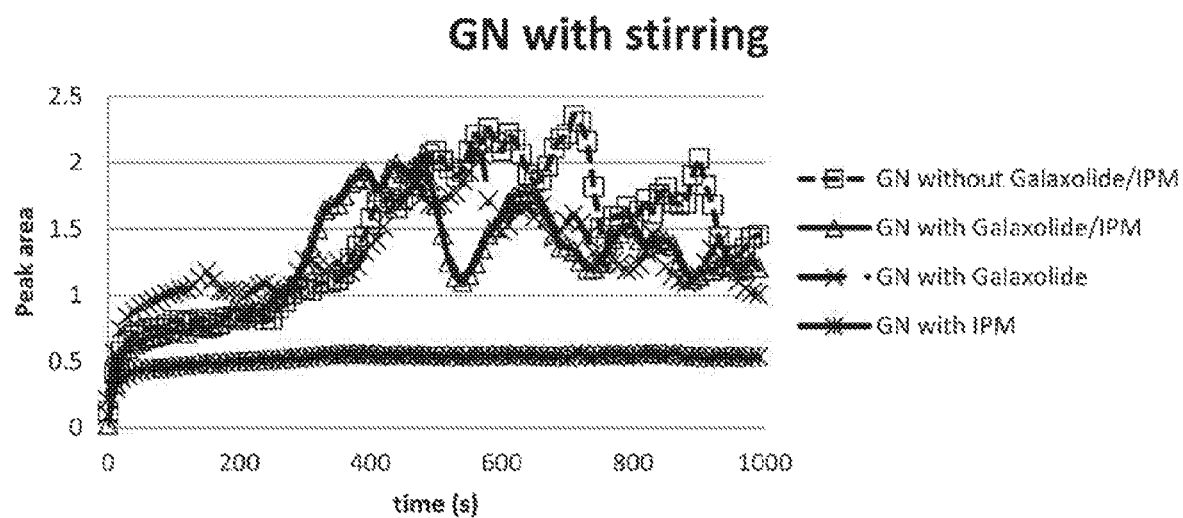
FIG. 7 shows the ammonia release kinetic of GN (tint) with Welloxon 6% with stirring.
Figure 8:
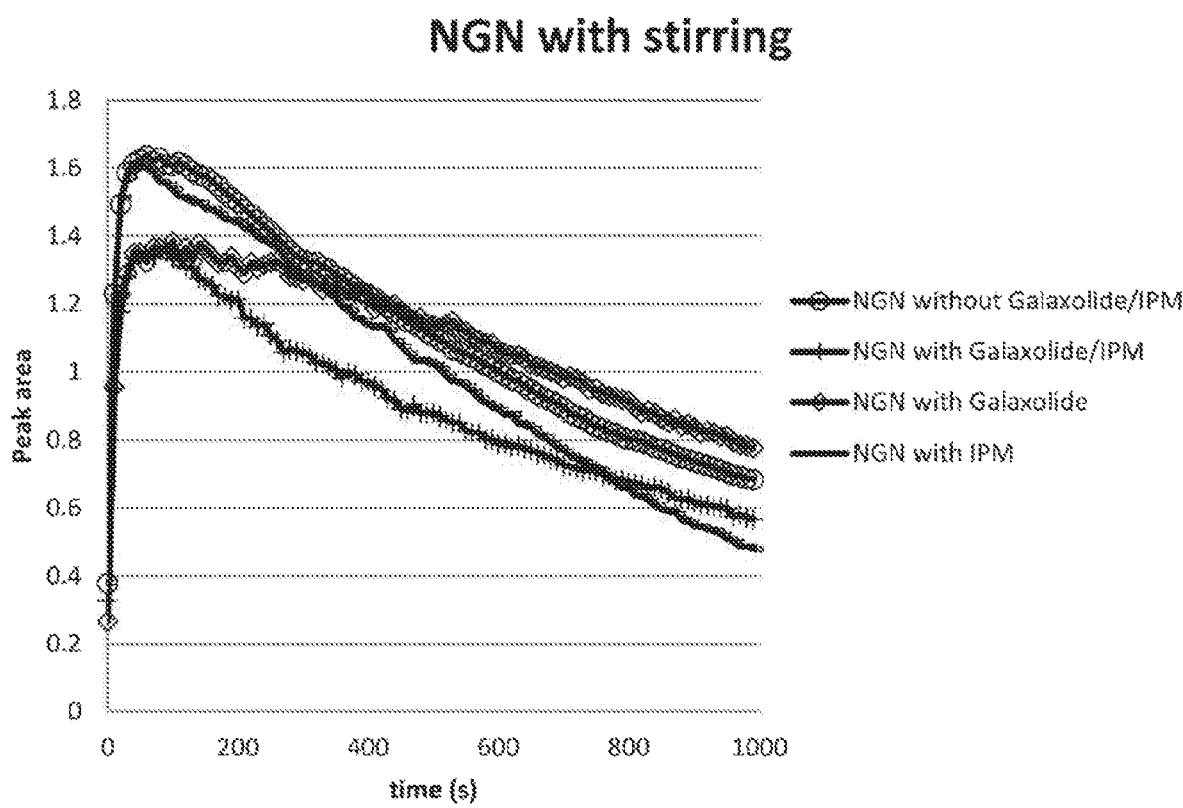
FIG. 8 shows the ammonia release kinetics of a NGN mixture with stirring.

The results of the measurements are shown in FIGS. 1 to 8. The absolute peak area values of different figures are not directly comparable and do not allow for a conclusion on an absolute effect. The peak area values of measurements within a single figure are directly comparable and do allow for a conclusion on an absolute effect.

The behavior of GN mixture is different as compared with the NGN mixture. The maximum of ammonia release is at the beginning of the kinetic curve (NGN mixture). That means at the beginning during mixing there is more free ammonia with the NGN mixture resulting in an immediate unpleasant malodor.

The maximum of ammonia release is at the middle of the kinetic curve (GN mixture). That means the ammonia smells later as with NGN and the exposition of the user is delayed and damped, resulting in a more pleasant experience.

Total Ammonia Release

Table 2 and Table 3 show the total ammonia content of the samples, analyzed via Kjeldahl (GCAS 58084429) and the total ammonia released within 1000 s measuring time. Every experiment consists of two measurements.

TABLE 2

Total ammonia release with stirring in the vessel

|  | NH3 solution | NH3/Galaxolide/IPM |
| --- | --- | --- |
| NH3 content % | 2.41 | 2.15 |
| NH3 content Released within 1000s % | 1.82 | 1.65 |
| Ratio % | 75.5 | 76.7 |

|  | GN without Galaxolide/IPM | GN with Galaxolide/IPM | GN with IPM | GN with Galaxolide |
| --- | --- | --- | --- | --- |
| NH3 content % | 2.41 | 2.52 | 2.09 | 2.14 |
| NH3 content Released within 1000s % | 0.93 | 0.85 | 0.29 | 0.76 |
| Ratio % | 38.6 | 33.7 | 13.9 | 35.5 |

|  | NGN without Galaxolide/IPM | NGN with Galaxolide/IPM | NGN with IPM | NGN with Galaxolide |
| --- | --- | --- | --- | --- |
| NH3 content % | 1.61 | 1.91 | 1.65 | 1.95 |
| NH3 content Released within 1000s % | 0.64 | 0.57 | 0.71 | 0.71 |
| Ratio % | 39.8 | 29.8 | 43.0 | 36.4 |

The examples show that the liquid crystalline Gel-Network nature of the aqueous component results in a significantly reduced release of ammonia at the presence of IPM alone as well as in the presence of Galaxolide or a mixture of IPM and Galaxolide. It is also shown that this effect cannot be observed for compositions without a liquid crystalline Gel-Network structure and that the effect of the presence of a single malodor suppressant such as IPM can even result in an increased release of ammonia. It further shows that, even in case of a comparable total release of ammonia, the release kinetics of the Gel-Network mixture (see FIG. 6) provide for a delayed release of Ammonia with simultaneous improvement of the perception of ammonia smell for the user.

TABLE 3

| | Paneltest | | |
|---|---|---|---|
| Tint | Developer | Mixing Ratio | Rating |
| GN | Welloxon | 1:1 | 1 |
| GN with Galaxolide | Welloxon | 1:1 | 0.5 |
| GN with Isopropylmyristate | Welloxon | 1:1 | 0.5 |
| NGN | Welloxon | 1:1 | 3-4 |
| NGN with Galaxolide | Welloxon | 1:1 | 3-4 |
| NGN with IPM | Welloxon | 1:1 | 3-4 |

0 = no Ammonia Smell
5 = Harsh Ammonia Smell

A paneltest was performed with 5 panelists with trained expertise in the classification of ammonia smells. The panelists received a mixture of tint and developer as described under GN and NGN above (stirred by a single operator for all tests until mixture was homogeneous). The panelists were asked to rate the ammonia smell according to a scale of 0 to 5, the mixture being passed from panelist to panelist with an additional stirring for each of the panelists.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed:

1. A hair coloring and/or bleaching composition comprising:
a first aqueous component (i) comprising one or more oxidizing agent(s) in a cosmetically acceptable carrier; and,
a second aqueous component (ii) comprising one or more alkalizing agent(s) comprising ammonia, its salts or mixtures thereof in a cosmetically acceptable carrier,
wherein the first aqueous component (i) and the second aqueous component (ii) are mixed in a ratio ranging from 5:1 to 1:5, and the total composition after mixing the first aqueous component (i) and the second aqueous component (ii) comprises:
   a) a linear and/or branched C12 to C30 fatty alcohol at from 0.5% to 20% relative to the total composition after mixing,
   b) one or more polyoxyethylene C12-C30 alkyl ether nonionic surfactants at from 0.1% to 5% relative to the total composition after mixing,
   c) a phosphate ester compound selected from the group consisting of alkyl phosphate ester, alkoxylated alkyl phosphate esters, and mixtures thereof at from 0.3% to 8% relative to the total composition after mixing;
   d) an anionic surfactant other than the phosphate ester at from about 1% or less relative to the total composition after mixing;
   e) optionally at least one oxidative dye precursor and at least one coupler or a mixture of two or more thereof;
wherein the first aqueous component (i) or the second aqueous component (ii) or both of the first aqueous component (i) and the second aqueous component (ii) comprise a gel-network system consisting of multi-lamellar sheets or vesicles or both, with d-spacing between 5 nm and 50 nm as measured by Small Angle X-Ray Scattering, and
wherein the first aqueous component (i) or the second aqueous component (ii) or both of the first aqueous component (i) and second aqueous component(ii) comprise a malodor suppressant consisting of isopropyl myristate.

2. The hair coloring and/or bleaching composition according to claim 1 wherein the total composition after mixing the first aqueous component (i) and the second aqueous component (ii) comprises
optionally from 0.5% to 30%, by total weight of the composition, of a fatty compound selected from the group consisting of mineral oil, hydrocarbon oil, and mixtures thereof.

3. The hair coloring and/or bleaching composition according to claim 1, wherein the linear and/or branched C12 to C30 fatty alcohol is selected from the group consisting of cetyl alcohol, stearyl alcohol, cetearyl alcohol, behenyl alcohol, and mixtures of two, three or more thereof.

4. The hair coloring and/or bleaching composition according to claim 1, wherein the one or more polyoxyethylene C12-C30 alkyl ether nonionic surfactants is selected from the group consisting of polyoxyethylene C12 to C30 alkyl ethers having at least 2 ethylene oxide units, polyoxyethylene C12 to C30 alkyl ethers having from 20 to 300 ethylene oxide units, polyoxyethylene C12 to C30 alkyl ethers having from 100 to 200 ethylene oxide units, ceteareth-25, steareth-20, steareth-100, steareth-150, steareth-200, and mixtures thereof.

5. The hair coloring and/or bleaching composition according to claim 1, wherein the composition comprises from 0.2% to 3% or from 0.3% to 1.5%, of one or more C12-C30 alkyl ether nonionic surfactants by total weight of the composition.

6. The hair coloring and/or bleaching composition according to claim 1, wherein the phosphate ester compound is selected from the group consisting of C12 to C30 alkyl phosphate esters, alkoxylated C12 to C30 alkyl phosphate esters, and mixtures thereof; alternatively from the group consisting of C12 to C18 alkyl phosphate esters, alkoxylated C12 to C18 alkyl phosphate esters, and mixtures thereof; alternatively from the group consisting of oleth-3 phosphate, oleth-5 phosphate, oleth-10 phosphate, cetoleth-5 phosphate, cetoleth-10 phosphate, trideceth-5 phosphate, trideceth-6 phosphate, trideceth-10 phosphate, cetyl phosphate, dicetyl phosphate, oleyl phosphate, dioleyl phosphate, stearyl phosphate, C9-15 alkyl phosphate, ceteareth-2 phosphate, ceteareth-20 phosphate, ceteth-10 phosphate, deceth-4 phosphate, glycereth-26 phosphate, PPG-5-ceteth-10 phosphate, steareth-2 phosphate, DEA-oleth-3 phosphate, DEA-oleth-3 phosphate, PEG-5 ethylhexyl ether phosphate, and mixtures thereof; alternatively from the group consisting of PPG-5-ceteth-10 phosphate, oleth-3 phosphate, oleth-10 phosphate, ceteth-10 phosphate, dicetyl phosphate, cetyl phosphate, stearyl phosphate, ceteareth-2 phosphate, and mixtures thereof; alternatively from the group consisting of ceteth-10 phosphate, dicetyl phosphate, ceteareth-2 phosphate, and mixtures thereof.

7. A hair coloring and/or bleaching composition according to claim 1, wherein the amount of isopropyl myristate is at least 0.1% by weight.

8. A hair coloring or bleaching composition according to claim 1, wherein the composition after mixing the first aqueous component (i) and the second aqueous component (ii) has a viscosity of from 150 to 2000 cPs.

9. A method of treating hair comprising the steps of applying a composition after mixing according to claim 1 to the hair, leaving said composition on the hair for from 2 to 60 minutes and subsequently rinsing said composition from the hair.

10. A method according to claim 9 wherein said composition is retained on the hair for a time period of less than 50 minutes.

11. A method of sequential oxidative hair coloring or hair bleaching comprising the steps of at least two sequential oxidative hair color or hair bleaching treatments, wherein the time period between each treatment is from 1 day to 60 days, and wherein each treatment comprises the steps of providing a composition according to claim 1, applying said composition to the hair, retaining said composition on the hair for a time period of less than 50 minutes and subsequently rinsing the composition from the hair.

12. A method for coloring and/or bleaching hair with a reduced or eliminated ammonia odor comprising applying the composition of claim 1 to hair.

13. A hair coloring or bleaching kit comprising
   An individually packaged first aqueous component (i) comprising, in a cosmetically acceptable carrier, one or more oxidizing agent(s) and
   An individually packaged second aqueous component (ii) comprising in a cosmetically acceptable carrier, one or more alkalizing agent(s) selected from the group consisting of ammonia, its salts and mixtures thereof,
   wherein the first aqueous component (i) or the second aqueous component (ii) or both the first aqueous component (i) and the second aqueous component (ii) comprise a gel-network system including multi-lamellar sheets or vesicles or both, with d-spacing between 5 nm and 50 nm as measured by Small Angle X-Ray Scattering, and the first aqueous component (i) or the second aqueous component (ii) or both comprise:
   a) a linear and/or branched C12 to C30 fatty alcohol,
   b) one or more polyoxyethylene C12-C30 alkyl ether nonionic surfactants,
   c) a phosphate ester compound selected from the group consisting of alkyl phosphate ester, alkoxylated alkyl phosphate ester, and mixtures thereof,
   d) less than 1% of an anionic surfactants other than phosphate esters and,
   wherein the first aqueous component (i) or the second aqueous component (ii) or both comprise a malodor suppressant of isopropyl myristate.

* * * * *